(12) United States Patent
Nishide et al.

(10) Patent No.: US 7,639,772 B2
(45) Date of Patent: Dec. 29, 2009

(54) IMAGE RECONSTRUCTING METHOD AND X-RAY CT APPARATUS

(75) Inventors: Akihiko Nishide, Tokyo (JP); Akira Hagiwara, Tokyo (JP); Kotoko Morikawa, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/539,343

(22) Filed: Oct. 6, 2006

(65) Prior Publication Data

US 2007/0121779 A1    May 31, 2007

(30) Foreign Application Priority Data

Oct. 7, 2005    (JP) .............................. 2005-295261

(51) Int. Cl.
*A61B 6/00* (2006.01)

(52) U.S. Cl. .......................................................... 378/4

(58) Field of Classification Search ............... 378/4–20, 378/901
See application file for complete search history.

(56) References Cited

U.S. PATENT DOCUMENTS

| | | | |
|---|---|---|---|
| 4,734,988 A | | 4/1988 | Steele et al. |
| 5,377,250 A | * | 12/1994 | Hu ............................... 378/15 |
| 5,654,820 A | | 8/1997 | Lu et al. ...................... 359/298 |
| 5,864,598 A | | 1/1999 | Hsieh et al. |
| 6,061,419 A | * | 5/2000 | Hsieh et al. ..................... 378/4 |
| 6,173,033 B1 | * | 1/2001 | Klingenbeck-Regn et al. ............................ 378/20 |
| 6,256,365 B1 | * | 7/2001 | Lai ................................ 378/4 |
| 6,272,200 B1 | * | 8/2001 | Pan et al. ....................... 378/15 |
| 6,343,108 B1 | * | 1/2002 | Heuscher ........................ 378/4 |
| 6,404,844 B1 | * | 6/2002 | Horiuchi et al. ................. 378/8 |
| 6,647,084 B1 | * | 11/2003 | Hsieh ............................ 378/4 |
| 6,845,144 B2 | | 1/2005 | Nishide et al. |
| 6,865,247 B2 | | 3/2005 | Hagiwara |

(Continued)

FOREIGN PATENT DOCUMENTS

JP    09-238935    *    9/1997

(Continued)

OTHER PUBLICATIONS

Kak, A.C. and Slaney, M., "Principles of Computerized Tomographic Imaging," IEEE Press, New York, (electronic copy, 1999) (93 pages).

*Primary Examiner*—Chih-Cheng G Kao
*Assistant Examiner*—Alexander H Taningco
(74) *Attorney, Agent, or Firm*—Armstrong Teasdale LLP

(57) ABSTRACT

The slice thickness of tomograms of an X-ray CT apparatus is to be kept as constant as practicable within an xy plane. In projected data before three-dimensional back-projection, after convolving row-directional filter of an X-ray detector whose filter coefficient is adjusted channel by channel, three-dimensional back-projection is performed to achieve image reconstruction thereby to control the slice thickness of tomograms according to the distance from the center of the xy plane. The slice thickness is controlled to keep it as constant as practicable independent of the distance from that center to regulate the picture quality of tomograms. Further, the relative density of distances on the reconstruction plane of X-ray detector data or projection data projected on the reconstruction plane is controlled by creating virtual projection data thereby to improve the picture quality of tomograms.

13 Claims, 23 Drawing Sheets

U.S. PATENT DOCUMENTS

| | | |
|---|---|---|
| 6,873,679 B2 | 3/2005 | Hagiwara |
| 6,977,984 B2 * | 12/2005 | Hsieh et al. .................... 378/4 |
| 2002/0122529 A1 * | 9/2002 | Heuscher ...................... 378/4 |
| 2002/0131549 A1 * | 9/2002 | Oikawa ........................ 378/19 |
| 2003/0016781 A1 | 1/2003 | Huang |
| 2003/0097063 A1 * | 5/2003 | Wang et al. ................. 600/425 |
| 2003/0185345 A1 * | 10/2003 | Hsieh .......................... 378/159 |
| 2004/0047449 A1 * | 3/2004 | Hagiwara .................. 378/98.8 |
| 2004/0081273 A1 | 4/2004 | Ning |
| 2004/0086075 A1 * | 5/2004 | Hein et al. ...................... 378/4 |
| 2005/0201511 A1 * | 9/2005 | Hagiwara et al. ............. 378/11 |
| 2005/0226365 A1 * | 10/2005 | Taguchi ....................... 378/13 |
| 2006/0093083 A1 * | 5/2006 | Nishide et al. ............... 378/17 |

FOREIGN PATENT DOCUMENTS

| | | |
|---|---|---|
| JP | 2002-320609 | 11/2002 |
| JP | 2003-159244 | 6/2003 |
| JP | 2003-334188 | 11/2003 |
| JP | 2004-041674 | 2/2004 |
| JP | 2004-041675 | 2/2004 |
| JP | 2004-073360 | 3/2004 |

* cited by examiner

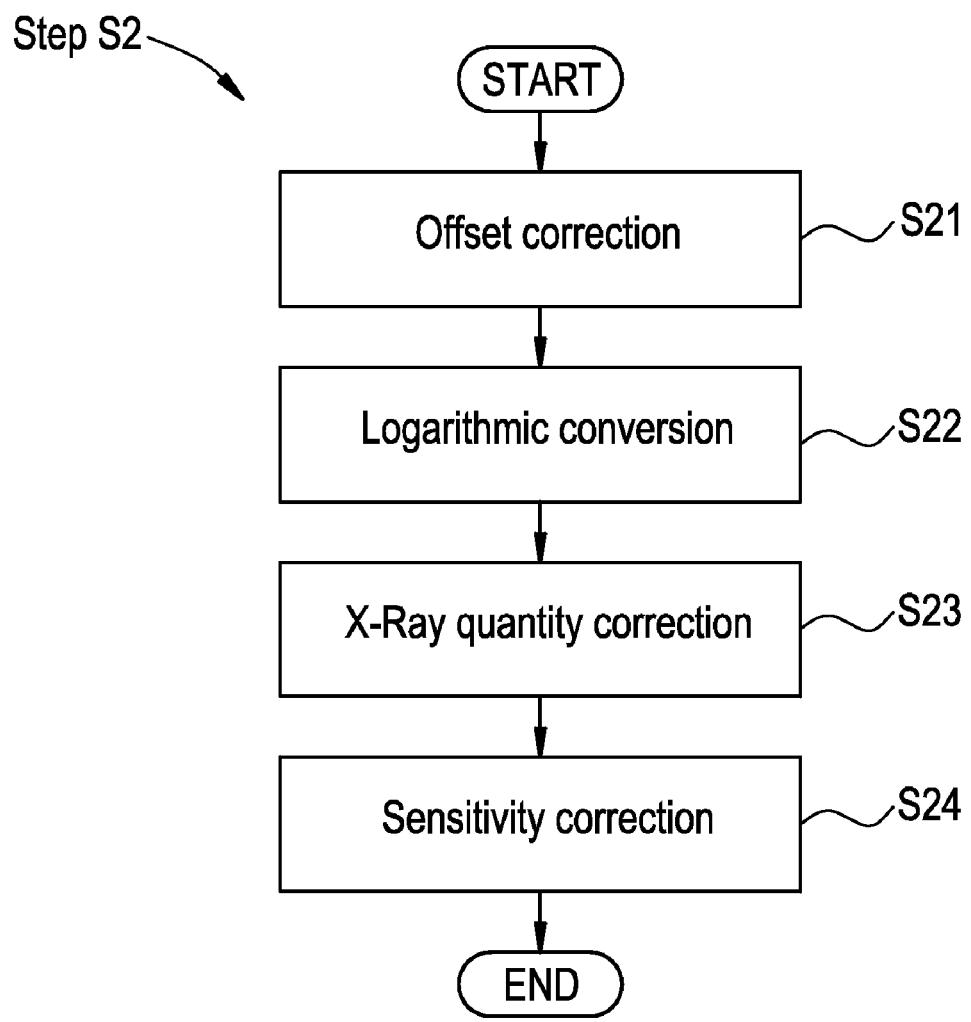

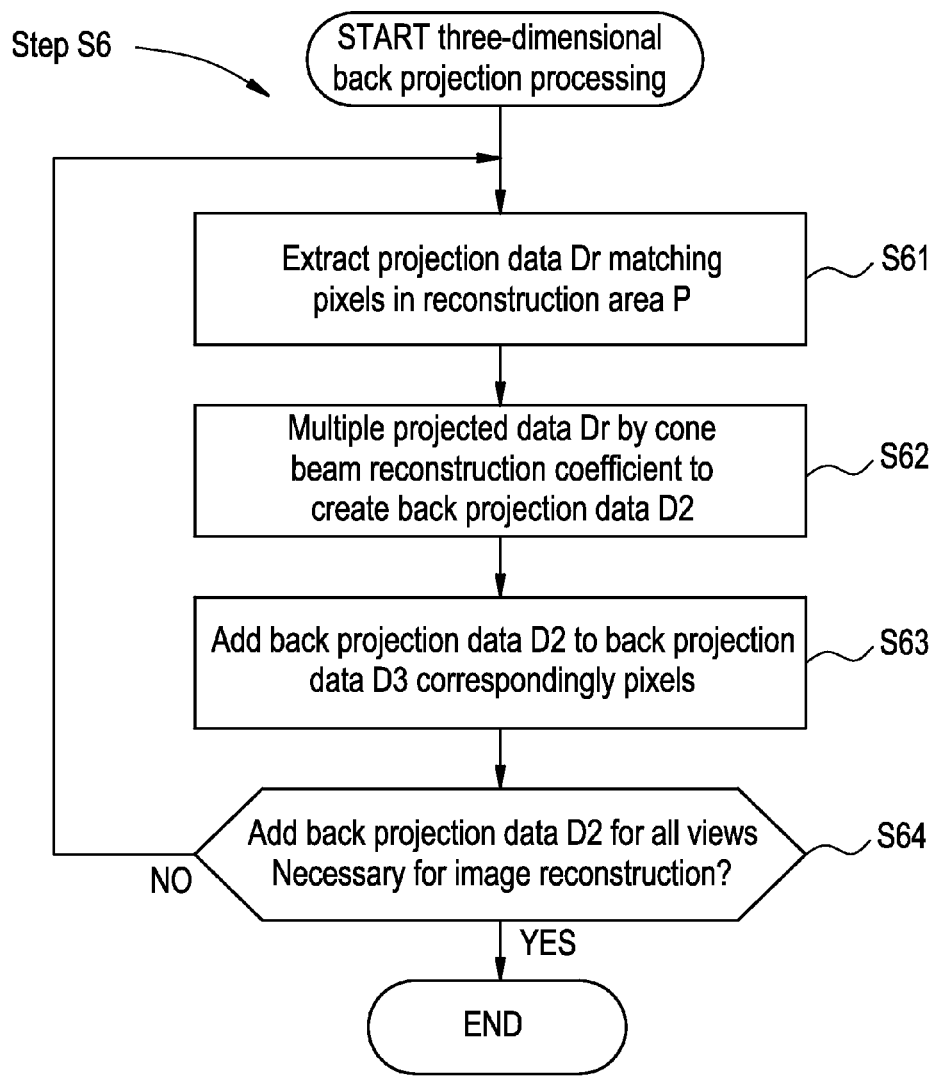

Reconstruction area

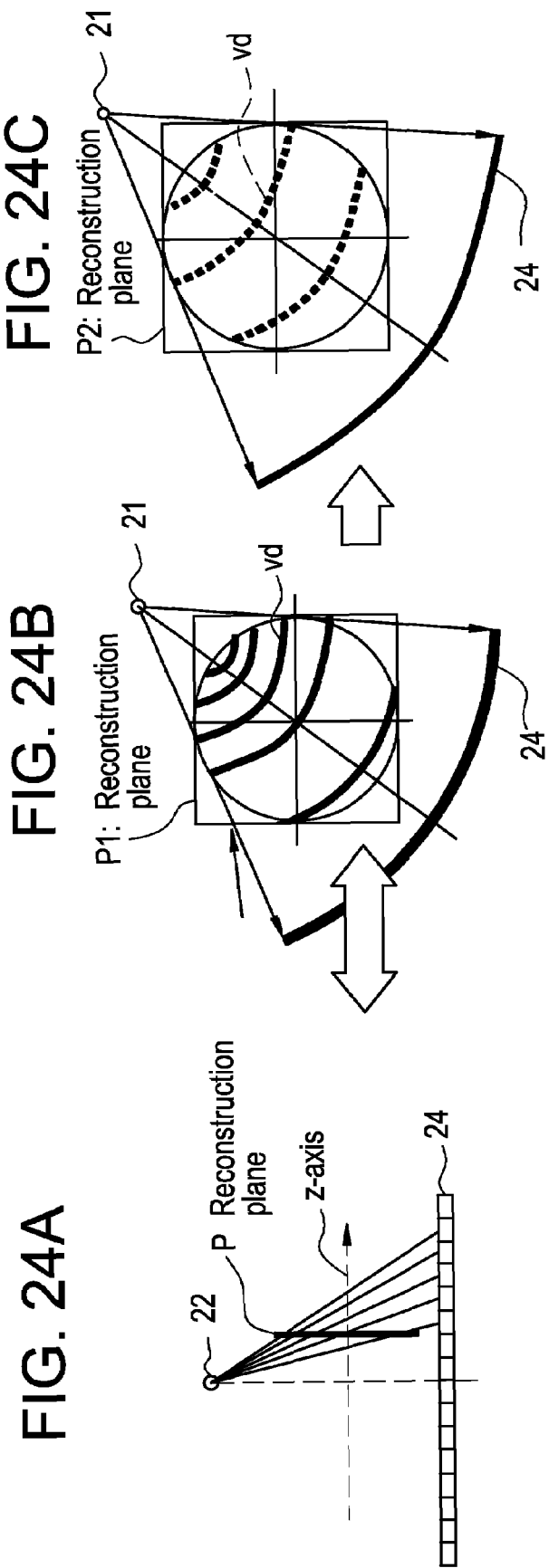

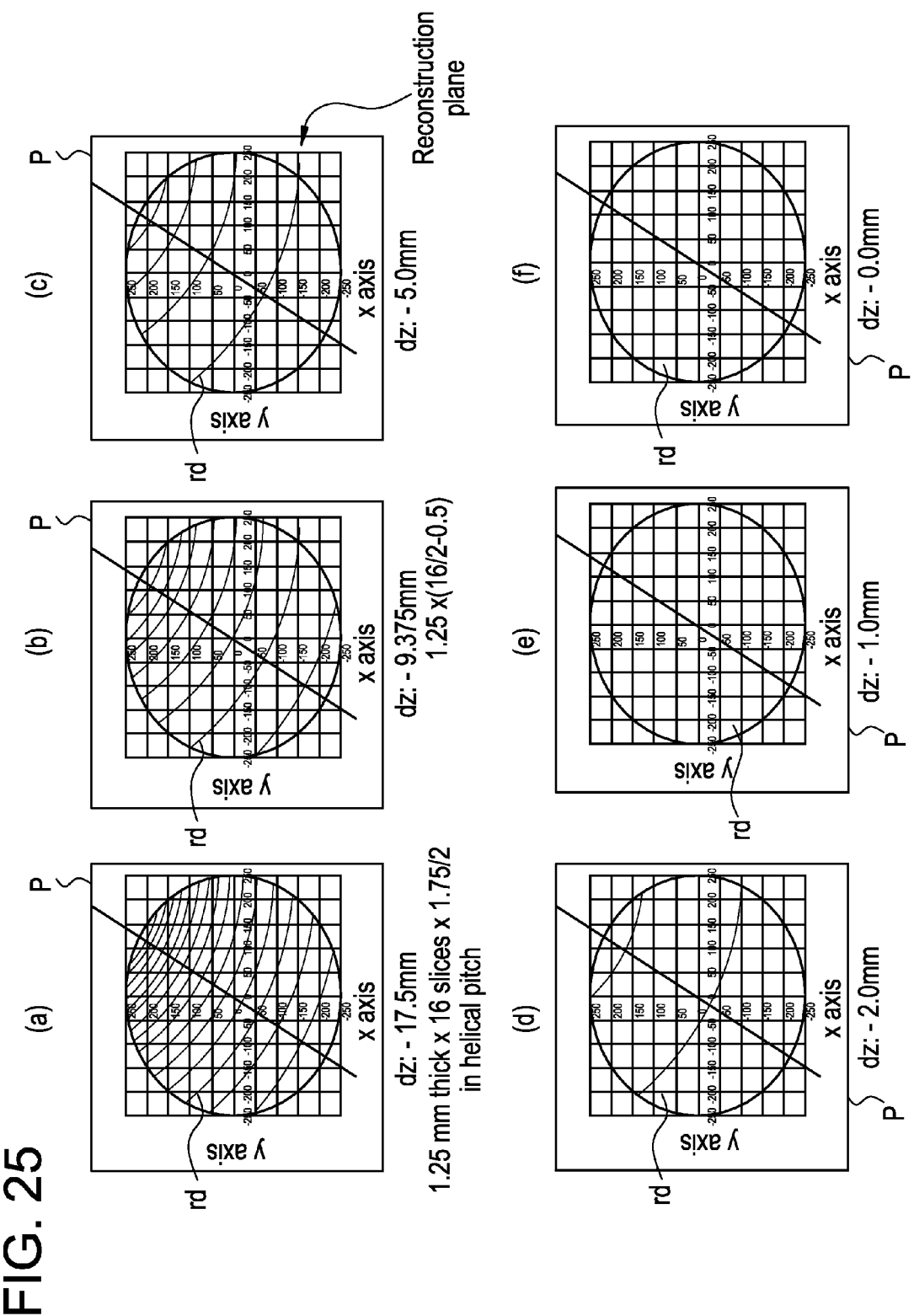

(a) Arciform projection data (in 30 degree direction) z-offcenter -14.58mm (b) Arciform projection data (in 210 degree direction) z-offcenter 2.92mm

IMAGE RECONSTRUCTING METHOD AND X-RAY CT APPARATUS

CROSS REFERENCE TO RELATED APPLICATIONS

This application claims the benefit of Japanese Application No. 2005-295261 filed Oct. 7, 2005.

BACKGROUND OF THE INVENTION

The present invention relates to an image reconstructing method for X-ray CT (Computed Tomography) apparatuses, for instance, and an X-ray CT apparatus.

When image reconstruction of projection data obtained by such as helical scanning, conventional scanning (axial scanning) and cine scanning (scanning of the same position in three directions a plurality of times to obtain tomograms at different points of time) based on a three-dimensional back projection method is to be accomplished, an X-ray CT apparatus is known which performs image reconstruction on the basis of intact projected data on each row of a multi-row detector (see JP-A No. 2001-for instance).

The apparatus of the above-described configuration was unable to perform control of slice thicknesses as consecutive values in the Z-direction, noise control or artifact control.

Regarding the slice thickness, it differs between the central part and the peripheral parts of image reconstruction, and it is impossible to control slice thicknesses in positions within the tomogram plane.

In three-dimensional image reconstruction by the X-ray CT apparatus, to calculate pixel data of the pixels of an image by using X-ray detector data corresponding to not only the X-direction but also the Z-direction, its hardware adaptation is considered, in order to be compatible with various applications which require specific pixels to have a plurality of rows of information, it is necessary to carry three-dimensional back-projection processing a plurality of times according to the quantity of that information. However, this is a redundant calculation.

Thus, image reconstruction hardware having no flexibility cannot freely back-project projection data of each row onto a given pixel.

For this reason, when a plurality of rows of projection data of different from that pixel are to be subjected to back projection processing, the back projection processing should be performed a plurality of times according to the geometrical condition of data collection for that plurality of rows of projection data (the positional relationship among the X-ray generation source, the X-ray detector and the subject).

In order to solve the problem noted above, what was considered necessary a three-dimensional image reconstruction algorithm which would permit back projection processing in one round by adding projection data of rows of different data collection geometries in a projection data space.

More specifically, as shown in FIG. 16 for instance, the spherical focus of an X-ray tube 21, an X-ray detector 24 and the X, Y and Z axes are defined. The X-ray tube 21 and the detector 24 shown in FIG. 16 rotate around the Z-axis.

FIG. 17 is a view of the configuration shown in FIG. 16 as seen in the direction of the X-axis. In other words, it is a YZ plane.

It has to be noted that this FIG. 17 shows one example of specific view time when an image is to be produced in a position away by ofz (off-center in z direction; also referred to as dz) from the center of the detector in the Z-direction at the time of conventional (axial) reconstruction or helical reconstruction.

The image position in which reconstruction is to be done in the direction of the Z-axis then as shown in FIG. 17 is represented by a reconstruction plane p. In FIG. 17, out of the straight lines L linking the X-ray focus of the X-ray tube 21 and the X-ray detector 24, only what passes the reconstruction plane p is shown.

Only the pixels on the reconstruction plane p which this straight line L passes are directly relevant to data detected by the detector 12, and data on all other pixels are created by weighted addition of detector data between which each such pixel is positioned.

FIG. 18 is a view of the reconstructed plane shown in FIG. 17 from the xy plane.

In more detail, pixels in the parts corresponding to equal distances from the X-ray tube 21 are directly relevant to X-ray detector data, and data on all other pixels are created by weighted addition of detector data between which each such pixel is positioned. One row of projection line of a multi-row X-ray detector having a curve such as what is shown in FIG. 18 will be referred to as real arciform projection data rd.

FIG. 19 is a diagram showing the geometrical relationship among virtual detector data vd, the X-ray focus, the detector and the reconstruction plane.

In the three-dimensional image reconstruction, the virtual detector data vd indicated by dotted lines as shown in FIG. 19 for instance are created from the real detector data rd indicated by solid lines as shown in FIG. 18 for instance. Thus, the virtual arciform projection data vd are created from the real arciform projection data rd.

These virtual projection data vd indicated by dotted lines can make it look as if data were collected in such a configuration.

Such virtual projection data vd indicated by dotted lines can be created from the real X-ray detector data rd indicated by solid lines by weighted addition processing or otherwise.

Viewed from the YZ plane, the virtual detector data vd indicated by dotted lines have a configuration such as shown in FIG. 20 for instance. Of viewed from the xy plane, they have a configuration such as shown in FIG. 21 for instance.

By creating the above-described virtual data vd from the real X-ray detector data rd by weighted addition processing or otherwise, inputting them as input data to three-dimensional image reconstruction hardware, and providing the three-dimensional image reconstruction hardware with information of such a virtualized detector configuration, data of the X-ray detector configuration as shown in FIG. 17 for instance, an image can be reconstructed in the X-ray detector configuration as shown in FIG. 20.

Further, where two reconstruction planes p1 and p2 are defined and added to each other as shown in FIG. 22 for instance, in three-dimensional image reconstruction three-dimensional image reconstruction is processed two times to reconstruct two images and those images are added.

However, it is redundant to perform three-dimensional image reconstruction two times. Since the addition can be accomplished in the projection data space, it is possible to reduce the processing quantity of three-dimensional image reconstruction.

In actual operation, regarding the reconstruction plane p1, the real arciform projection data rd are obtained as shown in FIGS. 23(a) and (b) for instance.

Regarding the reconstruction plane p2, the virtual arciform projection data vd are created as shown in FIGS. 24(a) and (c) for instance.

For instance, since the virtual arciform projection data vd shown in FIGS. 24(a) and (c) are so subjected to weighted addition as to be identical with the real arciform projection data rd shown in FIG. 23(b) and FIG. 24(b), it is possible to add the projections of the reconstruction planes p1 and p2 before the three-dimensional image reconstruction, and therefore the processing of three-dimensional image reconstruction to add the two reconstruction planes can be accomplished in one round.

Furthermore, as many planes of projection data can be added as desired, and it is also possible to use weighting to add them in any desired balance and thereby accomplish weighted addition. Similar effects can be obtained with parallel projection data as well.

Two problems will be discussed below.

[Problem iith Image Reconstruction Hardware without Flexibility]

As described above, in the hardware adaptation of three-dimensional image reconstruction, it is not possible to process three-dimensional back-projection by freely creating virtual arciform projection data from projection data of different rows in various patterns for each view.

In other words, what are compatible with a hardware adaptation of three-dimensional image reconstruction are general helical projection data or conventional (axial) projection data in which virtual arciform projection data are absent.

For such helical projection data, the moving speed of the table is figured out from the helical pitch information, the width of each X-ray detector in the Z-direction and the number of detector rows.

However, such items of information are fixed until the photographic conditions are once determined for a sequence of data, and the geometric system of three-dimensional image reconstruction is determined by the distance dz from the center of the detector row to the Z-position of the image to calculate and determine the parameters of three-dimensional image reconstruction.

The expression of that geometric system on the xy plane would be as shows in FIGS. 25(a) through (f) for instance. In FIGS. 25(a) through (f), for the sake of brevity of description, the rotating direction is expressed in a fixed angle, but in reality its right form is a state of having rotated by an equivalent of the angle in the rotational direction on the xy plane.

In the above-described case, dz in the Z-direction varies according to the view, and the position of one-row equivalent of arciform projection data matching the reconstruction plane on the xy plane varies according to that dz.

In other words, the greater the absolute value of dz, the denser the one-row equivalent of arciform projection data on the reconstruction plane p, and the smaller the value of dz, the sparser the data.

Thus in the three-dimensional image reconstruction hardware having no flexibility, the X-ray geometric system in each view is fixed by the given helical pitch, the thickness of the detector cells in the Z-direction and the number of slices.

Similarly in conventional (axial) scanning as well, its X-ray geometric system, namely the relative density of the arciform projection data on the reconstruction plane is fixed by dz.

Thus, arciform projection data cannot be effectively utilized in three-dimensional image reconstruction hardware (or software) with no flexibility of creating virtual arciform projection data as desired. As a result, no tomogram of adequate picture quality can be subjected to image reconstruction.

For this reason, there is a call for an apparatus which can reconstruction images of high accuracy by using arciform projection data on image reconstruction hardware (or software).

[Inconsistency in Weighting of Back Projection Processing by Feldkamp Reconstruction Method]

Incidentally, in a common three-dimensional image reconstruction algorithm or a common Feldkamp image reconstruction algorithm, there is a problem of inconsistency in the weighting of the cone beam reconstruction weighting coefficient. This is due to the relative density of arciform projection data dependent on the value of dz as stated above.

In more detail, in an image reconstruction algorithm which uses opposed data by subjecting weighted addition to the opposed data, it does so by subjecting to weighted addition data to be projection on pixels on the reconstruction plane by using data differing in phase by 180 degrees. There will arise an inconsistency unless the sum of different weighting functions at the time of creation by weighted addition is 1.0, resulting in an inconsistency in the uniformity of artifacts and CT values on the tomogram.

For instance, pixels which have no direct match in the arciform projection data rd on the reconstruction plane p shown in FIG. 25 and are positioned between the arciform projection data rd are created by weighted addition from the arciform projection data rd between which the pixels are positioned.

When the weighting function of the cone beam reconstruction weighting coefficient at the time varies steeply, if there is a different in relative density from the opposed data, the sum of weighting functions of pixels will differ from 1.0. This results in an inconsistency in weighting.

Description will be made with reference to FIG. 26. As shown therein, pixels positioned between arciform projection data with weighted addition are subjected to image reconstruction after creation by weighted addition with the arciform projection data between which the pixels are positioned. Therefore, if the weighting function of the cone beam reconstruction weighting coefficient is already applied to the arciform projection data, the weighting coefficient of the cone beam reconstruction weighting coefficient is also figured out by weighted addition at the same time.

If this weighted addition is linear weighted addition and the weighting function of the original cone beam reconstruction weighting coefficient is nonlinear, there will arise a difference from the linear weighted addition, resulting in an inconsistency.

Where, for instance, weighting with the cone beam reconstruction weighting coefficient is calculated for each pixel at the time of three-dimensional image reconstruction or weighted addition similar in shape to the weighting function is done, there will arise no inconsistency, but such processing would require complex three-dimensional image reconstruction processing. Thus, the load of calculation would become too great to be realistic.

For this reason, a common Feldkamp image reconstruction algorithm involves the problem of inconsistency with respect to weighting.

An object of the present invention is to improve the problems noted above and provide an image reconstructing method and an X-ray CT apparatus for the processing of three-dimensional image reconstruction capable of achieving image reconstruction of tomograms of high picture quality or image reconstruction of tomograms of desired picture quality.

SUMMARY OF THE INVENTION

The invention makes it possible to control, regarding projection data before three-dimensional back-projection, the slice thickness of tomograms according to the distance from the center of the xy plane by convolving a filter in the detector row direction (z-direction) whose coefficient is adjusted for each channel or keeping the slice thickness as constant as practicable irrespective of the distance from the center.

According to the first aspect, the invention provides an image reconstructing method for reconstructing a tomogram based on projection data collected by a multi-row X-ray detector for detecting X-rays radiated from the X-ray generating device, the image reconstructing method comprising: a first step of convolving row-directional filter on said projection data; a second step of convolving a reconstructing function on said data obtained by said first step; and a third step of reconstructing by performing three-dimensional back-projection process based on data obtained by said second step.

By the image reconstructing method according to the first aspect described above, the slice thickness can be controlled by convolving row-directional filter on projection data and the capability to control the slice thickness permits improvement in terms of noise and artifacts.

According to the second aspect, the invention provides an image reconstructing method for reconstructing a tomogram based on projection data collected by a multi-row X-ray detector for detecting X-rays radiated from the X-ray generating device, the image reconstructing method comprising: a first step of convolving a reconstructing function on said projection data; a second step of convolving row-directional filter on the data obtained by said first step; and a third step of reconstructing by performing three-dimensional back-projection process based on the data obtained by said second step.

By the image reconstructing method according to the second aspect, the slice thickness can be controlled by convolving row-directional filter after convolving the reconstructing function, and the capability to control the slice thickness permits improvement in terms of noise and artifacts.

According to the third aspect, the invention provides the image reconstructing method according to the first or second aspect characterized in that data are collected by conventional scanning (axial scanning), helical scanning or cine scanning.

By the image reconstructing method according to the third aspect described above, the slice thickness can be controlled by conventional scanning (axial scanning), helical scanning or cine scanning alike or by convolving row-directional filter after convolving the reconstructing function, and the capability to control the slice thickness permits improvement in terms of noise and artifacts.

According to the fourth aspect, the invention provides the image reconstructing method according to any of the first through third aspects characterized in that a filter coefficient of the row-directional filtering differs from one channel to another of the multi-row X-ray detector.

By the image reconstructing method according to the fourth aspect described above, when subjecting projection data to row-directional filtering, the difference of a filter coefficient of the row-directional filtering from one channel to another enables the slice thickness to be equal between the center and the peripheries of reconstruction. Also, the capability to control the slice thickness permits improvement in terms of noise and artifacts.

According to the fifth aspect, the invention provides the image reconstructing method according to any of the first through fourth aspects characterized in that a filter coefficient of the row-directional filtering differs from one row to another of the multi-row X-ray detector.

By the image reconstructing method according to the fifth aspect described above, since row-directional filter different in filter coefficient from one row to another can be convolved, especially in conventional scanning (axial scanning), adjustment of picture quality by differences in the X-ray cone angle can be performed.

According to the sixth aspect, the invention provides the image reconstructing method according to any of the first through fifth aspects characterized in that the filter coefficient of the row-directional filtering is deconvolution filtering.

By the image reconstructing method according to the sixth aspect described above, since deconvolution row-directional filter is convolved row by row, the slice thickness of each row can be thinned.

According to the seventh aspect, the invention provides the image reconstructing method according to any of the first through sixth aspects characterized in that, when the three-dimensional back-projection processing is to be accomplished, weighted addition in the row direction by linear weighted addition, multi-point weighted addition or weighted addition with a nonlinear weighted addition coefficient is processed.

By the image reconstructing method according to the seventh aspect, when weighted addition in the row direction is to be accomplished by multi-point weighted addition or weighted addition with a nonlinear weighted addition coefficient, "picture quality improvement of tomograms", "control the slice thickness to be thin" and the like are made possible.

According to the eighth aspect, the invention provides the image reconstructing method according to any of the first through seventh aspects characterized in that, when the three-dimensional back-projection processing is to be done, projection data of an X-ray detector row virtualized to the projection data by the X-ray detector are created by weighted addition or row-directional filtering, and three-dimensional back-projection processing is accomplished also covering the projection data of the virtualized X-ray detector row created by the weighted addition.

By the image reconstructing method according to the eighth aspect, since the projection data of the virtualized detector row are created by weighted addition or row-directional filtering and three-dimensional image reconstruction is performed, actual and virtual rows of X-ray detector data or projection data can be accurately multiplied by cone beam weighting coefficients, resulting in tomograms of high picture quality.

According to the ninth aspect, the invention provides the image reconstructing method according to the eighth aspect by which, when the three-dimensional back-projection processing is to be done, processing is so performed that, if the projection data of the X-ray detector and the virtual projection data created by weighted addition or row-directional filtering of the virtualized X-ray detector are matched with the reconstruction plane in combination, the interval on the reconstruction plane where projection data combining projection data in a given direction and the virtual projection data are matched is substantially equal to the interval on the reconstruction plane where projection data combining projection data in a direction opposed by 180 degrees and the virtual projection data.

By the image reconstructing method according to the ninth aspect described above, since it is possible to make the interval of combined real and virtual projection data in a given direction on the reconstruction plane substantially equal to the interval of those in a direction opposed thereto in 180 degrees on the reconstruction plane, the sum of cone beam reconstruction weighting coefficients, namely the sum of data in one direction and those in a direction opposed thereto in 180 degrees, is kept approximately to one all the time, there is no inconsistency in weighting function, and the tomograms undergoing three-dimensional reconstruction are reduced in artifacts, also resulting in improved uniformity of CT values within the reconstruction plane.

According to the tenth aspect, the invention provides the image reconstructing method according to the eighth aspect characterized in that the total number of projection data rows combining the number of projection data of the X-ray detector rows and the number of projection data of the virtualized X-ray detector rows is optimized in each projecting direction (view direction) and 180 degrees to the projecting direction or the direction opposed by substantially 180 degrees.

By the image reconstructing method according to the tenth aspect described above, since the total number of projection data rows combining the number of projection data of the X-ray detector rows and the number of projection data of the virtualized X-ray detector rows is optimized in each projecting direction (view direction) and 180 degrees to the projecting direction or the direction opposed by substantially 180 degrees, tomograms of high picture quality can be obtained in a short image reconstruction period.

According to the eleventh aspect, the invention provides the image reconstructing method according to the eighth aspect characterized in that all the projecting directions (view directions) are unified in each projecting direction (view direction) at the maximum of the total number of projection data rows combining the number of projection data of the X-ray detector rows and the number of projection data of the virtualized X-ray detector rows.

By the image reconstructing method according to the eleventh aspect described above, since the total number of projection data rows combining the number of projection data of the X-ray detector rows and the number of projection data of the virtualized X-ray detector rows in each projecting direction (view direction) is matched with the maximum in each projecting direction, tomograms of high picture quality can be obtained.

According to the twelfth aspect, the invention provides an X-ray CT apparatus having X-ray generating device; a multi-row X-ray detector which detects X-rays radiated from the X-ray generating device; data collecting device which collects projection data by rotating the X-ray generating device and the multi-row X-ray detector around a center of rotation between the X-ray generating device and the multi-row X-ray detector; row-directional filtering device for convolving row-directional filter on the projection data collected by said data collecting device; reconstruction convolving device for convolving a reconstructing function on the projection data obtained said row-directional filtering device; and back-projecting device for reconstructing a tomogramic view by three-dimensional back projecting the projection data obtained processing by said reconstruction convoluting device.

In the X-ray CT apparatus according to the twelfth aspect described above, the slice thickness can be controlled by convolving row-directional filtering on projection data, and the capability to control the slice thickness permits improvement in terms of noise and artifacts.

According to the thirteenth aspect, the invention provides an X-ray CT apparatus characterized in that it consists of so-called data collecting device for an X-ray CT apparatus, which can collect X-ray data by causing a multi-row X-ray detector corresponding to X-ray generating device to rotate around a center of rotation between them; reconstruction convolving device for convolving a reconstructing function on the projection data collected by said data collecting device; row-directional filtering device for convolving row-directional filter in the row direction based on the projected data obtained by said reconstruction convoluting device; and back-projecting device for reconstructing a tomogramic view by three-dimensional back projecting the projection data obtained processing by said row-directional filtering device.

In the X-ray CT apparatus according to the thirteenth aspect described above, the slice thickness can be controlled by convolving row-directional filter after the convolution of a reconstructing function, and the capability to control the slice thickness permits improvement in terms of noise and artifacts.

According to the fourteenth aspect, the invention provides the X-ray CT apparatus according to the twelfth or thirteenth aspect characterized in that data collection is accomplished by conventional scanning, helical scanning or cine scanning.

In the X-ray CT apparatus according to the fourteenth aspect described above, the slice thickness can be controlled by row-directional filtering after pre-treatment or after the convolution of a reconstructing function similarly by any of conventional scanning, helical scanning and cine scanning, and the capability to control the slice thickness permits improvement in terms of noise and artifacts.

According to the fifteenth aspect, the invention provides the X-ray CT apparatus according to any of the twelfth through fourteenth aspects characterized in that a filter coefficient of the row-directional filter differs from one channel to another.

In the X-ray CT apparatus according to the fifteenth aspect described above, the slice thickness can be controlled to be the same between the central part and the peripheral parts of image reconstruction because the filter coefficient of the row-directional filterdiffers from one channel to another in subjecting the projection data to row-directional filter, and the capability to control the slice thickness permits improvement in terms of noise and artifacts.

According to the sixteenth aspect, the invention provides the X-ray CT apparatus according to any of the twelfth through fifteenth aspects characterized in that a filter coefficient of the row-directional filter differs from one row to another.

In the X-ray CT apparatus according to the sixteenth aspect described above, since row-directional filter different in filter coefficient from one row to another can be convoluted, especially in conventional scanning (axial scanning), adjustment of picture quality by differences in the X-ray cone angle can be performed.

According to the seventeenth aspect, the invention provides the X-ray CT apparatus according to any of the twelfth through sixteenth aspects characterized in that a filter coefficient of the row-directional filter is deconvolution filter.

In the X-ray CT apparatus according to the seventeenth aspect described above, since row-directional filter is deconvolved on each row, the slice thickness of each row can be thinned.

According to the eighteenth aspect, the invention provides the X-ray CT apparatus according to any of the twelfth through seventeenth aspects characterized in that the back-projecting device processes weighted addition in the row direction by linear weighted addition, multi-point weighted addition or weighted addition with a nonlinear weighting coefficient.

In the X-ray CT apparatus according to the eighteenth aspect described above, when weighted addition in the row direction is to be accomplished by multi-point weighted addition or weighted addition with a nonlinear weighted addition coefficient, "picture quality improvement of tomograms", "control to keep the slice thickness thin" and the like are made possible.

According to the nineteenth aspect, the invention provides the X-ray CT apparatus according to any of the twelfth through eighteenth aspects characterized in that, when the three-dimensional back-projection processing is to be done, projection data of an X-ray detector row virtualized to the projection data by the X-ray detector are created by weighted addition or row-directional filtering.

In the X-ray CT apparatus according to the nineteenth aspect described above, since the projection data of a virtualized detector row are created by weighted addition or row-directional filtering and three-dimensional image reconstruction is performed, actual and virtual rows of X-ray detector data or projection data can be accurately multiplied by cone beam weighting coefficients, resulting in tomograms of high picture quality.

According to the twentieth aspect, the invention provides the X-ray CT apparatus according to the nineteenth aspect characterized in that, when the three-dimensional back-projection processing is to be done, if the projection data of the X-ray detector and the virtual projection data created by weighted addition or with a z-filter are matched with the reconstruction plane in combination, the interval on the reconstruction plane where projection data combining projection data in a given direction and the virtual projection data are matched is substantially equal to the interval on the reconstruction plane where projection data combining projection data in a direction opposed by 180 degrees and the virtual projection data.

In the X-ray CT apparatus according to the twentieth aspect described above, since it is possible to make the interval of combined real and virtual projection data in a given direction on the reconstruction plane substantially equal to the interval of those in a direction opposed thereto in 180 degrees on the reconstruction plane, the sum of cone beam reconstruction weighting coefficients, namely the sum of data in one direction and those in a direction opposed thereto in 180 degrees, is kept approximately to 1 all the time, there is no inconsistency in weighting function, and the tomograms undergoing three-dimensional reconstruction are reduced in artifacts, also resulting in improved uniformity of CT values within the reconstruction plane.

According to the twenty-first aspect, the invention provides the X-ray CT apparatus according to the nineteenth aspect characterized in that the total number of projection data rows combining the number of projection data of the X-ray detector rows and the number of projection data of the virtualized X-ray detector rows is optimized in each projecting direction (view direction) and 180 degrees to the projecting direction or the direction opposed by substantially 180 degrees.

According to the twenty-first aspect described above, since the total number of projection data rows combining the number of projection data of the X-ray detector rows and the number of projection data of the virtualized X-ray detector rows is optimized in each projecting direction (view direction) and 180 degrees to the projecting direction or the direction opposed by substantially 180 degrees, tomograms of high picture quality can be obtained in a short image reconstruction period.

According to the twenty-second aspect, the invention provides the X-ray CT apparatus according to the twentieth aspect characterized in that all the projecting directions are unified in each projecting direction(view direction) at the maximum of the total number of projection data rows combining the number of projection data of the X-ray detector rows and the number of projection data of the virtualized X-ray detector rows.

According to the twenty-second aspect described above, since the total number of projection data rows combining the number of projection data of the X-ray detector rows and the number of projection data of the virtualized X-ray detector rows in each projecting direction (view direction) is matched with the maximum in each projecting direction, tomograms of high picture quality can be obtained.

According to the present invention, an image reconstructing method and an X-ray CT apparatus for the processing of three-dimensional image reconstruction capable of achieving image reconstruction of tomograms of high picture quality or image reconstruction of tomograms of desired picture quality can be provided.

Further, the image reconstructing method and the X-ray CT apparatus according to the invention, enables the slice thickness of tomograms to be controlled according to the distance from the center of the xy plane, which is the reconstruction plane, by so-called row-directional filtering.

Also, the slice thickness can be kept as constant as practicable irrespective of the distance from the center.

This provides the effects of improvement in terms of noise and artifacts. There is a further effect of thinning the slice thickness by deconvolution z-filtering.

Further, the invention is characterized in that, in performing three-dimensional back projection, projection data of a detector row virtualized to the projection data by an X-ray detector are created by weighted addition or z-directional filtering. There is another effect of improving picture quality by a three-dimensional reconstructing method characterized in that, when projection data having undergone convolution processing with a reconstructing function are to be subjected to three-dimensional back-projection, where the projection data of a real X-ray detector and the virtual projection data created by weighted addition or with a z-filter by a virtual X-ray detector are matched with the reconstruction plane in combination, the interval on the reconstruction plane where projection data combining projection data in a given direction and the virtual projection data are matched is substantially equal to the interval on the reconstruction plane where the combined real and virtual projection data in a direction opposed by 180 degrees.

Also, arciform projection data can be created in any desired position in three-dimensional image reconstruction hardware (or software) with no freedom of creating virtual arciform projection data.

Further, the relative density of distances between different data when virtual arciform data are projected on the reconstruction plane can be controlled.

It is also possible to uniformize the relative density of distances between different data when the virtual arciform projection data of opposed data are projected on the reconstruction plane.

The aforementioned three effects makes it possible to secure flexibility for various applications, which are adaptations of three-dimensional image reconstruction even in three-dimensional image reconstruction hardware (or software) with no freedom.

Further by controlling the relative density of virtual arciform projection data, the inconsistency of weighting of three-dimensional image reconstruction in a conventional three-dimensional image reconstruction algorithm or Feldkamp image reconstruction algorithm can be reduced. Thus the accuracy of image reconstruction is enhanced, resulting in improved picture quality.

Further, by securing flexibility for applications, the z-filter technique realized in conventional non-three-dimensional image reconstruction can be now realized as row-directional filtering in three-dimensional image reconstruction not only in helical scanning but also in conventional scanning (axial scanning) or cine scanning. This enables a reduction in artifacts and improvement with respect to noise to be realized.

Whereas three-dimensional back-projection of one rotation or more is needed when data of one rotation or more are used to perform three-dimensional image reconstruction, since data of the same angle can be integrated or subjected to weighted addition in the projection data space according to the invention, three-dimensional image reconstruction of data of one rotation or more can be achieve in one rotation of three-dimensional back-projection.

Also, since projection data differing by 180 degrees or 360 degrees in phase, if they are parallel, can be integrated or subjected to weighted addition in the projection data space, image reconstruction of data of a half rotation or more can be accomplished by a half rotation of back-projection.

Further, for not only helical data but also conventional data, when reconstruction in a specific dz position is to be done, by replacing real arciform projection data with virtual arciform projection data of any desired dz or helical data of any desired pitch, it is made possible to control the relative density of virtual arciform projection data and reduce inconsistency regarding weighting.

Also, conventional data can be subjected to row-directional filtering.

BRIEF DESCRIPTION OF THE DRAWINGS

FIG. 1 is a block diagram of an X-ray CT apparatus in one mode for carrying out the present invention.

FIG. 2 is a drawing for describing the rotation of the X-ray tube and the multi-row X-ray detector.

FIG. 3 is a flow chart showing the outline of the operations by the X-ray CT apparatus in one mode for carrying out the invention.

[FIG. 4] FIG. 4 is a flow chart showing details of the pre-treatment.

[FIG. 5] FIG. 5 is a flow chart showing details of the three-dimensional image reconstruction processing.

[FIG. 6]

FIG. 7 is a conceptual diagram showing the lines projected on the detection plane.

FIG. 8 is a conceptual diagram showing the state data DT(view, x, y) projected on the reconstruction area.

FIG. 9 is a conceptual diagram showing the back-projection pixel data D2 of pixels on the reconstruction area.

FIG. 10 is a drawing for describing the state in which back-projection data D3 are obtained by all-view adding the back-projection pixel data D2 correspondingly to pixels.

[FIG. 11]

[FIG. 12]

FIG. 14 is a diagram showing a tomogram in a peripheral part subjected to row-directional filtering where the slice thickness is greater and a tomogram whose slice thickness is uniformized by row-directional filtering.

[FIG. 15]

FIG. 16 is a diagram showing the X-ray geometric system.

FIG. 17 is a diagram showing the X-ray detector and the reconstruction plane as viewed in the X-axis direction.

FIG. 18 is a diagram showing the reconstruction plane and the arciform projection data projected from the X-ray detector.

FIG. 19 is a diagram showing the reconstruction plane and the real arciform projection data and virtual arciform projection data projected from the X-ray detector.

FIG. 20 is a diagram showing the reconstruction plane and the X-ray detector.

FIG. 21 is a diagram showing the reconstruction plane and the virtual arciform projection data.

FIG. 22 is a diagram showing plural-image addition in the projection data space.

[FIG. 23]

[FIG. 24] FIGS. 24a, 24b, and 24c are diagrams showing the reconstruction plane p2.

[FIG. 25] FIGS. 25a, 25b, 25c, 25d, 25e, and 25f are diagrams showing the reconstruction plane and the virtual arciform projection data.

FIG. 26 is a diagram for describing inconsistencies between opposed data and cone beam weighting coefficients.

FIGS. 27a, 27b, and 27c are diagrams showing the conceptual drawings of differences in density between sets of mutually opposed data.

FIGS. 28a, 28b, 28c, and 28d are diagrams showing the conceptual drawings of differences in density between sets of arciform projection data.

FIG. 29 is a diagram showing a case in which inconsistencies between opposed data and cone beam weighting coefficients are reduced.

FIGS. 30a and 30b are diagrams showing opposed sets of arciform projection data equal in density.

FIGS. 31a, 31b, 31c, and 31d are diagrams showing the conceptual drawings of arciform projection data.

DETAILED DESCRIPTION OF THE INVENTION

One mode for carrying out the present invention will be described in detail below with reference to drawings. Incidentally, this is nothing to limit the invention.

Figure 1:
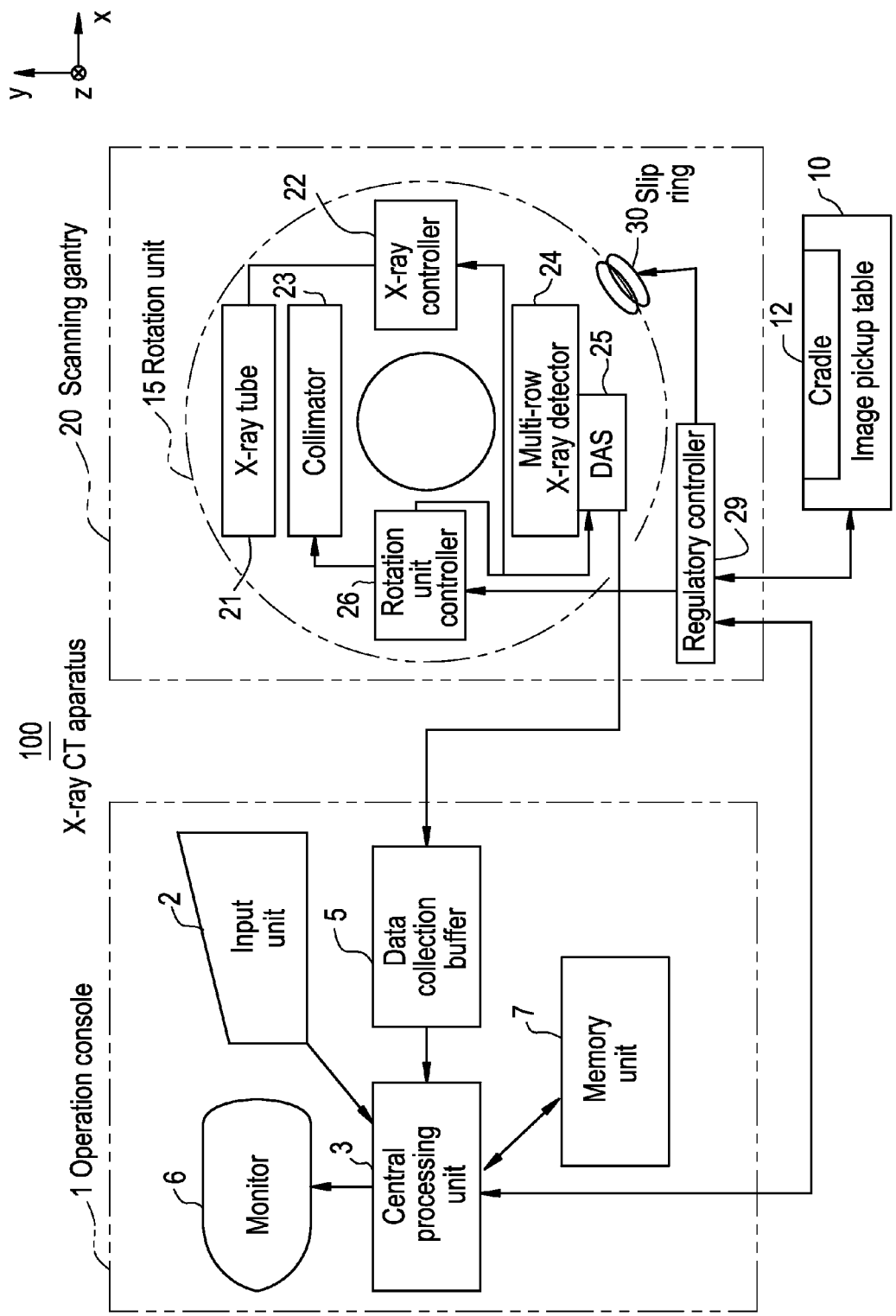
[FIG. 1]

FIG. 1 is a configurational block diagram of an X-ray CT apparatus in one mode for carrying out the invention.

An X-ray CT apparatus 100 in this mode for carrying out the invention is equipped with an operation console 1, an image pickup table 10 and a scanning gantry 20.

The operation console 1 is equipped with an input unit 2 for accepting inputs by the operator, a central processing unit 3 for executing image reconstruction processing and the like pertaining to the invention, a data collection buffer 5 for collecting projection data acquired by the scanning gantry 20, a monitor 6 for displaying CT images reconstructed from the projection data, and a memory unit 7 for storing programs, data and X-ray CT images.

The image pickup table unit 10 is equipped with a cradle 12 which, mounted with a subject, moves in and out of a bore (hollow part) in the scanning gantry 20. The cradle 12 is lifted, lowered and moved linearly with the table by a motor built into the table unit 10.

The scanning gantry 20 is equipped with an X-ray tube 21, an X-ray controller 22, a collimator 23, a multi-row X-ray detector 24 which detects X-rays radiated from the X-ray tube 21, a DAS (Data Acquisition System) 25, a rotation controller 26 which controls the X-ray tube 21, the multi-row X-ray detector 24 and the like around a center of rotation between the X-ray tube 21 and the multi-row X-ray detector 24 or in more detail around the body axis of the subject, and a regulatory controller 29 which exchanges control signals and the like with the operation console 1 and the image pickup table 10.

The X-ray tube 21 corresponds to one example of X-ray generating device pertaining to the invention, and the multi-row X-ray detector 24 corresponds to one example of multi-row X-ray detector pertaining to the invention. The multi-row X-ray detector 24 may be a planar X-ray detector.

Figure 2:
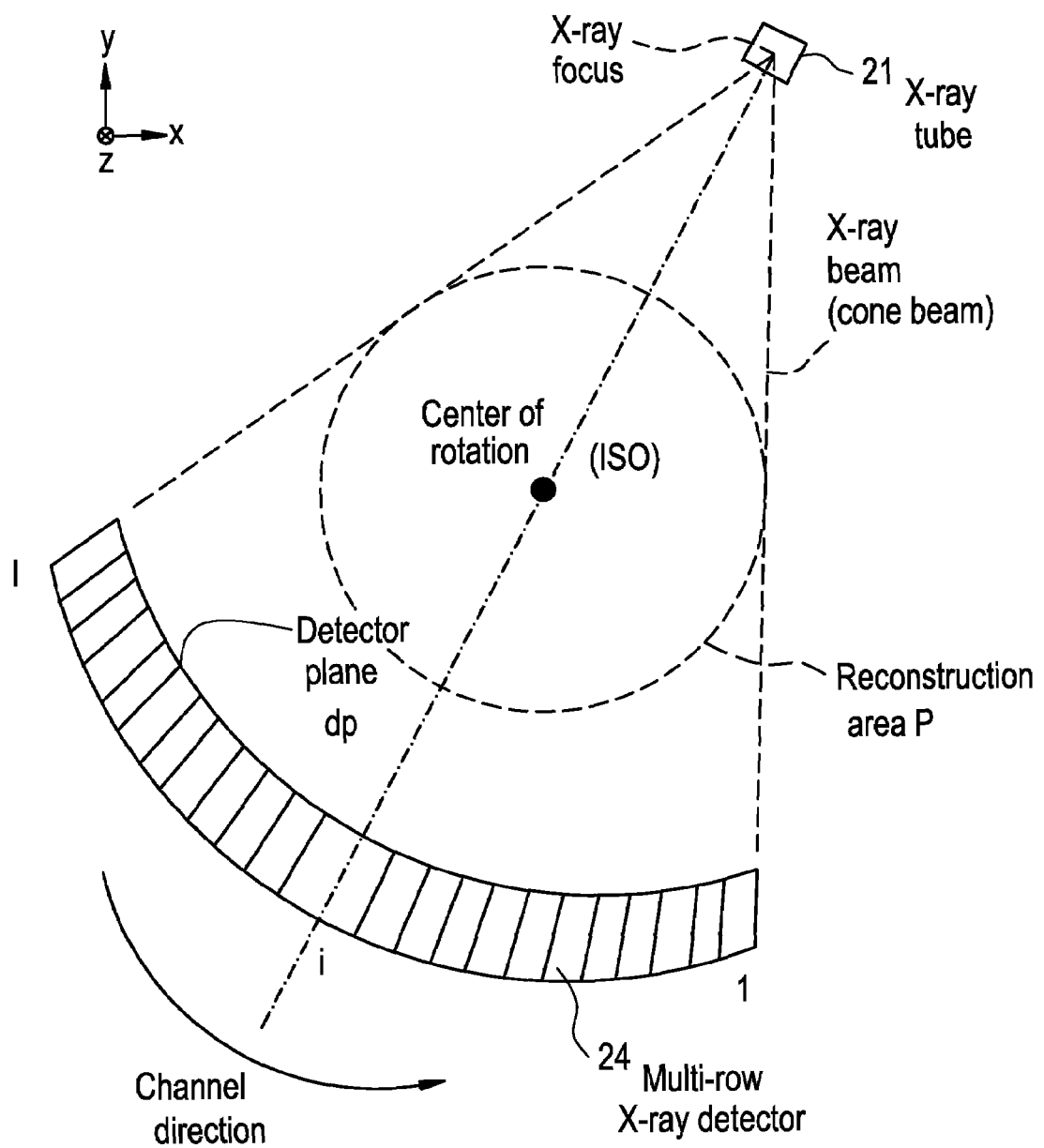
[FIG. 2]

FIG. 2 is a drawing for describing the geometric arrangement of the X-ray tube 21 and the multi-row X-ray detector 24.

For instance, the X-ray tube 21 and the multi-row X-ray detector 24 rotate around a center of rotation IC.

The vertical direction being denoted as the y-direction, the horizontal direction, as the x-direction, and a table proceeding direction orthogonal thereto, as the z-direction, the plane of rotation of the X-ray tube 21 and the multi-row X-ray detector 24 is the xy plane. The moving direction of the cradle 12 is the z-direction.

The X-ray tube 21 generates an X-ray beam referred to as a cone beam CB. When the direction of the center axis of the cone beam CB is parallel to the y-direction, the view angle is supposed to be 0°.

The multi-row X-ray detector 24 has 256 detector rows for instance. Each of the detector rows has 1024 channels for instance.

Projection data collected by irradiation with X-rays undergo A/D conversion by the DAS 25 from the multi-row X-ray detector 24, and are inputted to the data collection buffer 5 via a slip ring 30. The data inputted to the data collection buffer 5 undergo image reconstruction processing pertaining to the invention by the CPU (Central Processing Unit) 3 in accordance with a program in the memory unit 7 to generate an image, which is displayed on the monitor 6.

Figure 3:
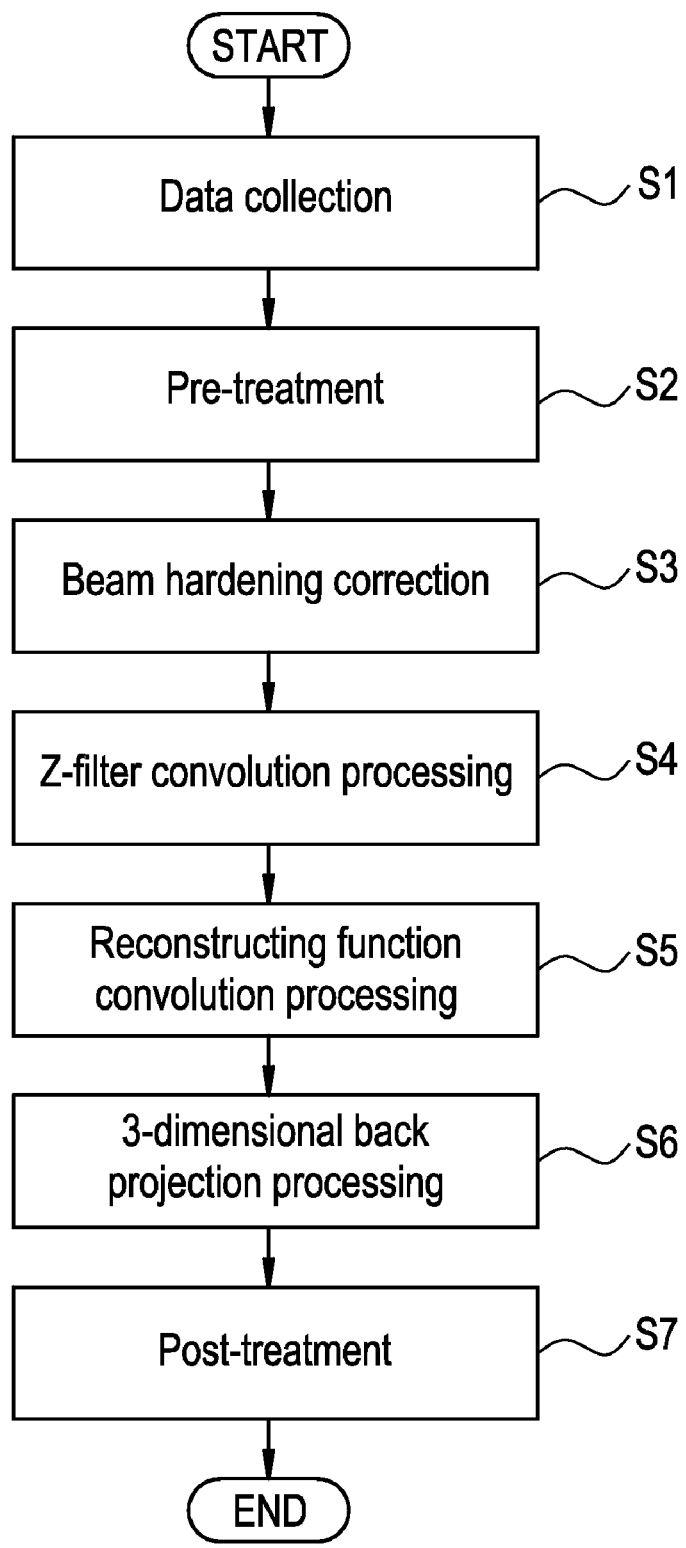
[FIG. 3]

FIG. 3 is a flow chart showing the outline of the operations by the X-ray CT apparatus 100. The operations pertaining to the invention will be described below, focusing on the operations of the central processing unit 3 while referring to FIG. 3.

At step S1, the X-ray tube 21 and the multi-row X-ray detector 24 are rotated around the object of photography and, when the cradle 12 is to be helically scanned, projection data D0 (view, j, i) represented by a view angle view, a detector row number j and a channel number i are collected while the table is linearly moved.

In the case of conventional scanning (axial scanning), projection data D0 (view, j, i) are collected while the table is kept still. (Regarding this data collection processing, description will be made afterwards with reference to FIG. 4 through FIG. 12.)

At step S2, projection data D0 (view, j, i) are subjected to pre-treatment. The pre-treatment consists of, for instance, step S21 of offset correction, step S22 of logarithmic conversion, step S23 of X-ray quantity correction and step S24 of sensitivity correction as shown in FIG. 4.

At step S3, pre-treated projection data D1 (view, j, i) are subjected to beam hardening correction. In beam hardening correction S3, the projection data having undergone sensitivity correction S4 of pre-treatment S2 being represented by D11 (view, j, i) and the data after the beam hardening correction S3 being represented by D11 (view, j, i), is expressed in a polynomial form for instance as represented by Mathematical Expression (1) below.

[Mathematical Expression 1]

$$D11(\text{view}, j, i) = D1(\text{view}, j, i) \cdot \\ (B_0(j, i) + B_1(j, i) \cdot D1(\text{view}, j, i) + B_2(j, i) \cdot D1(\text{view}, j, i)^2) \quad (1)$$

Since each j row of detectors can be subjected to independent beam hardening correction then, if the tube voltages of different data collection systems are different under the photographic conditions, the differences in X-ray energy characteristics of detectors from row to row can be compensated for.

At step S4, projection data D11 (view, j, i) having undergone beam hardening correction are subjected to z-filter convolution processing, by which filtering in the z-direction is applied.

Figure 12A:
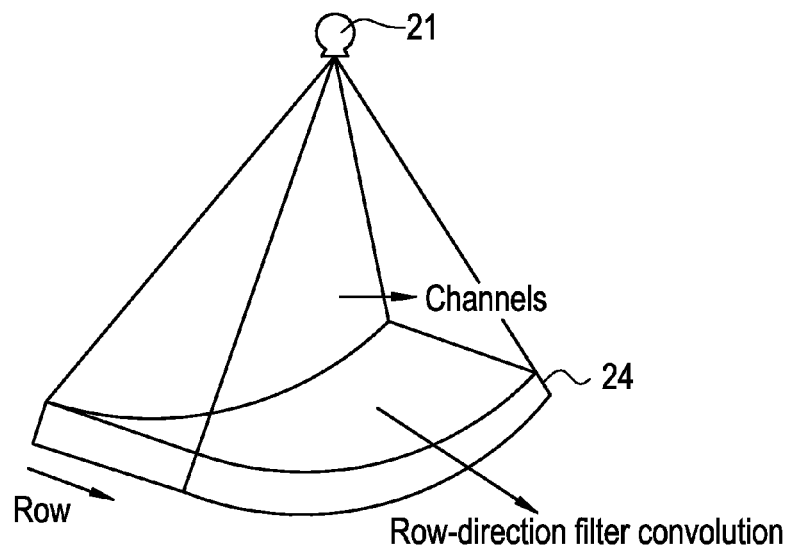
FIGS. 12a and 12b are drawings for describing row-directional filtering convolution.
Figure 12B:
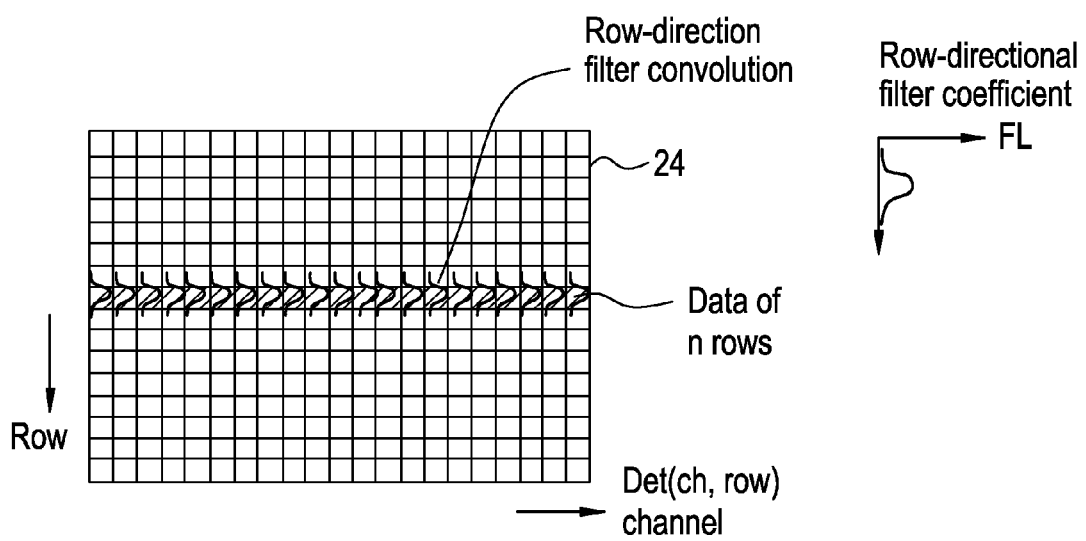

Thus at step S4, as shown in FIG. 12(a), the slice thickness can be controlled by varying the number of filters of the row-directional filtering. In this case, as shown in FIG. 12(b), a row-directional filtering coefficient is convoluted on each row of X-ray projection data. As shown in FIGS. 12, after the pre-treatment at each view angle and in each data collection system, the projection data of the multi-row X-ray detector D11 (view, j, i) (i=1 to CH, j=1 to ROW) having undergone beam hardening correction are subjected in the row direction to filtering whose row-directional filtering size is five rows, such as (w1(i), w2(i), w3(i), w4(i) and w5(i)) for instance.

Here, the sum of the filter coefficients is 1 as indicated by Mathematical Expression (2).

[Mathematical Expression 2]

$$\sum_{k=1}^{5} w_k(i) = 1 \quad (2)$$

The corrected detector data D12 (view, j, i) are as indicated by Mathematical Expression (3) below.

[Mathematical Expression 3]

$$D12(\text{view}, j, i) = \sum_{k=1}^{5} (D11(\text{view}, j+k-3, i) \cdot w_k(j)) \quad (3)$$

Incidentally, the maximum value of a channel being represented by CH and the maximum value of a row, by ROW, Mathematical Expressions (4) and (5) will hold.

[Mathematical Expression 4]

$$D11(\text{view},-1,i)=D11(\text{view},0,i)=D11(\text{view},1,i) \quad (4)$$

[Mathematical Expression 5]

$$D11(\text{view, ROW}, i)=D11(\text{view, ROW}+1,i)=D11(\text{view, ROW}+2,i) \quad (5)$$

Figure 13A:
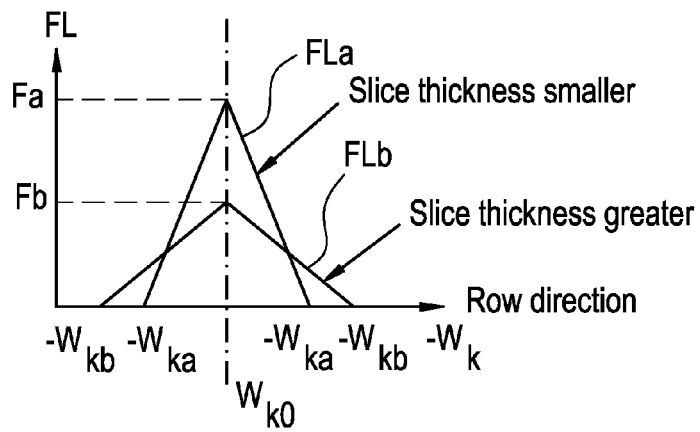
[FIG. 13] FIG. 13 includes diagrams showing the relationship between the row-directional filtering coefficient and slice thickness.

In further detail, when the slice thickness is to be thinned, as shown in FIG. 13(a) for instance, row-directional filtering FLa is used of which the filter coefficient FL of row-directional filtering is a first magnitude Fa in the central position Wk0 of the X-ray detector 24 in the row direction and decreases in proportion to the distance from the central position Wk0 until it becomes 0 at a distance Wka.

When the slice thickness is to be increased, as shown in FIG. 13 (a) for instance, row-directional filtering FLb is used of which the filter coefficient FL of row-directional filtering is a second magnitude Fb, which is smaller than the first magnitude Fa, in the central position Wk0 of the X-ray detector 24 in the row direction and decreases in proportion to the distance from the central position Wk0 until it becomes 0 at a distance Wkb, which is greater than the distance Wka.

Figure 15A:
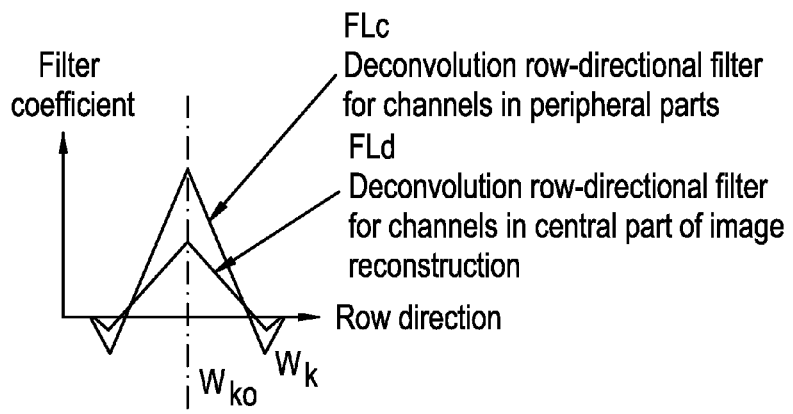
FIGS. 15a, 15b, and 15c are diagrams showing deconvolution row-directional filtering for channels in a peripheral part and deconvolution row-directional filtering for channels in the central part of reconstruction.
Figure 15B:
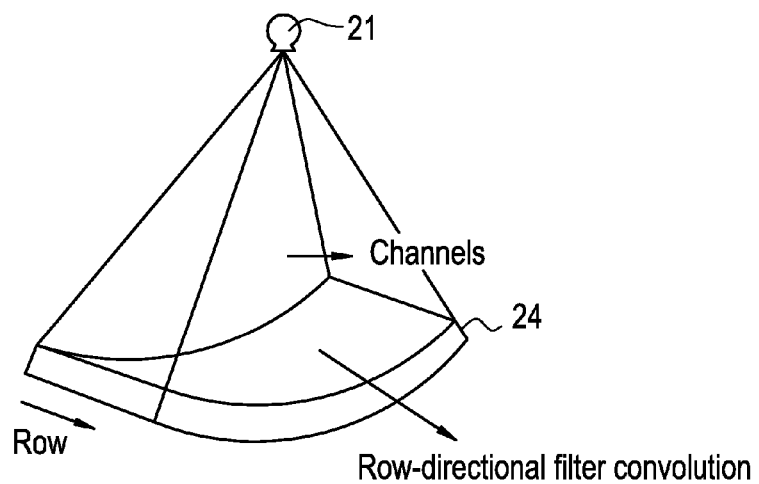
Figure 15C:
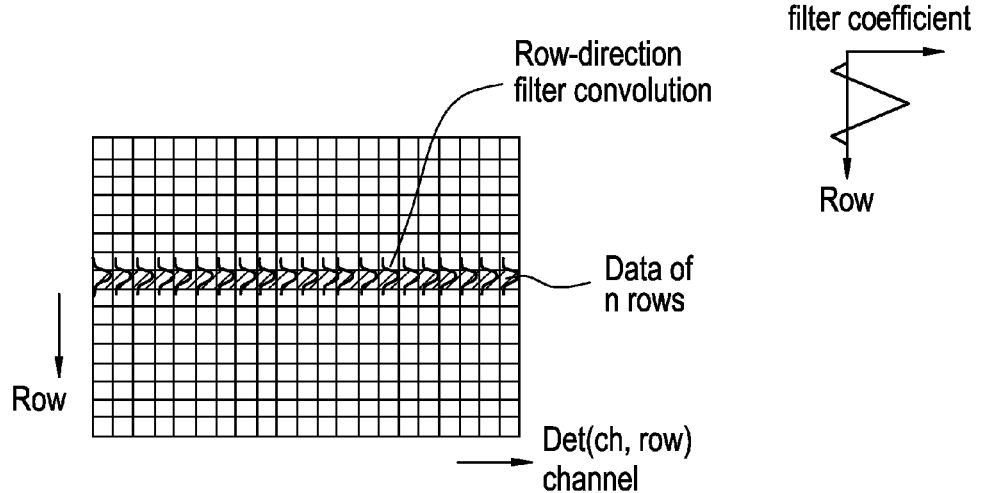
Figure 16:
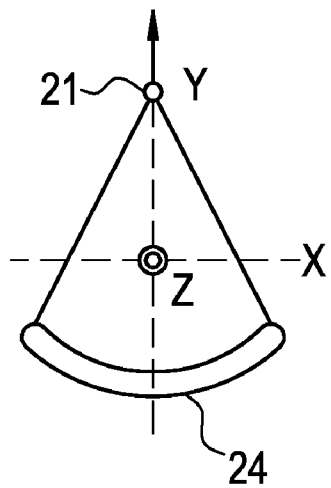
[FIG. 16]
Figure 17:
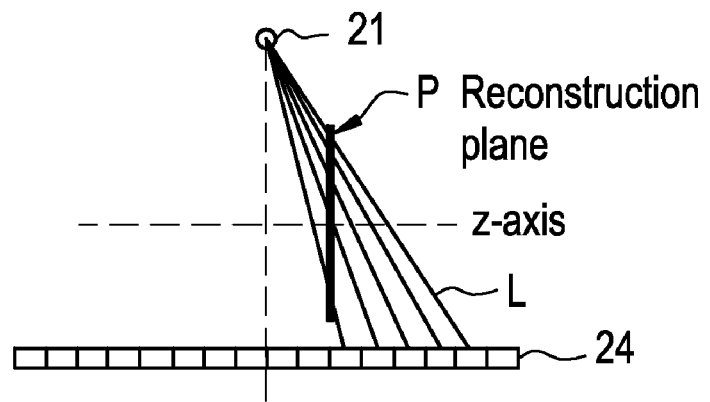
[FIG. 17]
Figure 18:
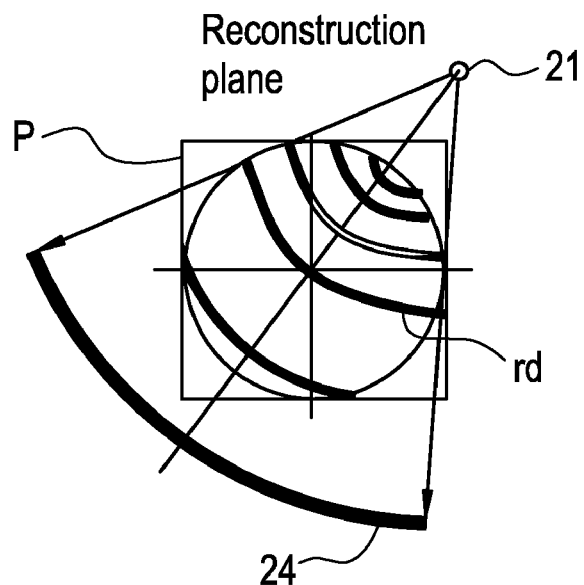
[FIG. 18]
Figure 19:
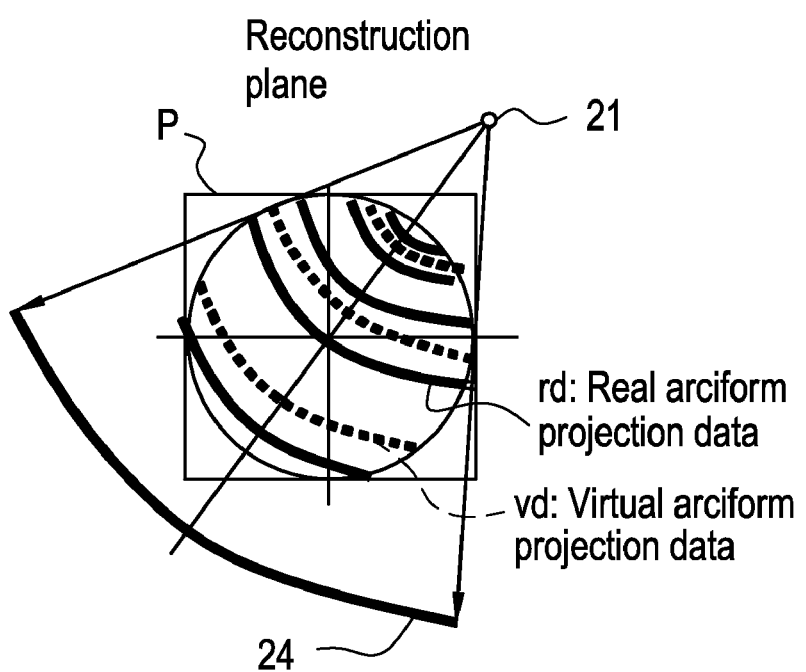
[FIG. 19]
Figure 20:
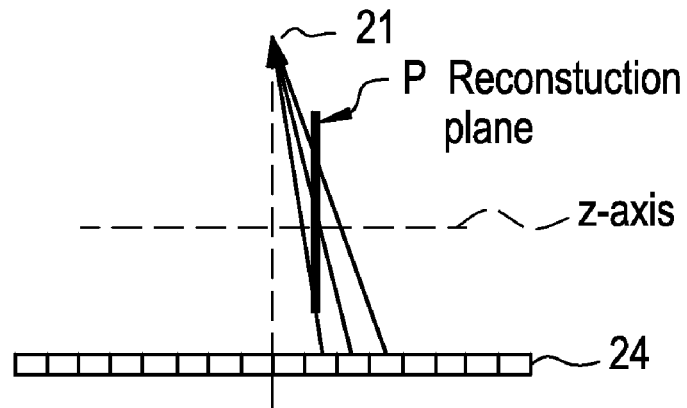
[FIG. 20]
Figure 21:
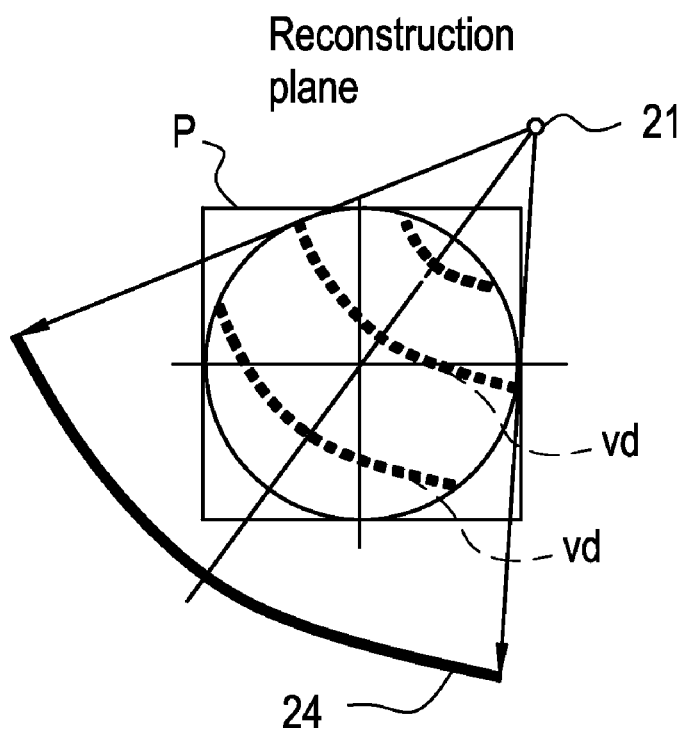
[FIG. 21]
Figure 22:
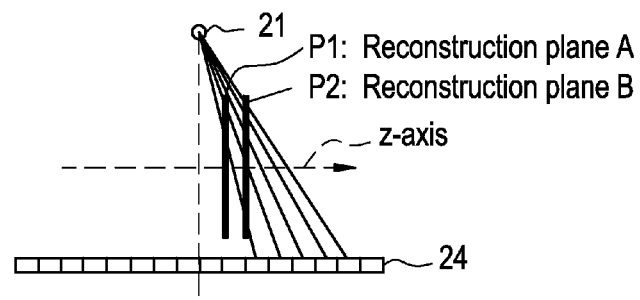
[FIG. 22]
Figure 23A:
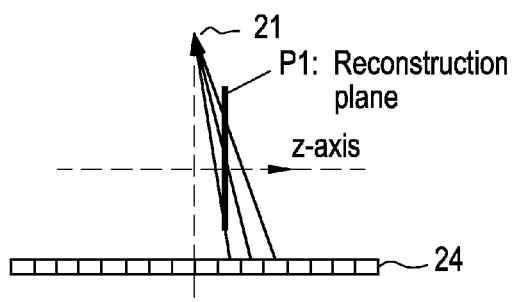
FIGS. 23a and 23b are diagrams showing the reconstruction plane p1.
Figure 23B:
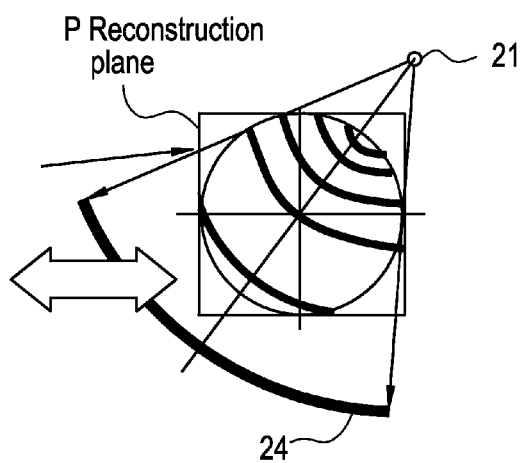

As another mode for carrying out the invention, as shown in FIGS. 15(a) through (c) for instance, a tomogram of a thinner slice thickness can be realized by subjecting the filter coefficient of row-directional filtering to deconvolution filtering.

In more detail, as shown in FIGS. 15(a) through (c) for instance, projection data from channels in the peripheral part of the X-ray detector 24 are subjected to deconvolution row-directional filtering processing FLc having a filter coefficient which steeply varies near the central position Wk0, and projection data from channels in the central part of reconstruction are subjected to deconvolution row-directional filtering processing FLd having a filter coefficient lower than in the deconvolution row-directional filtering processing FLc.

Figure 14:
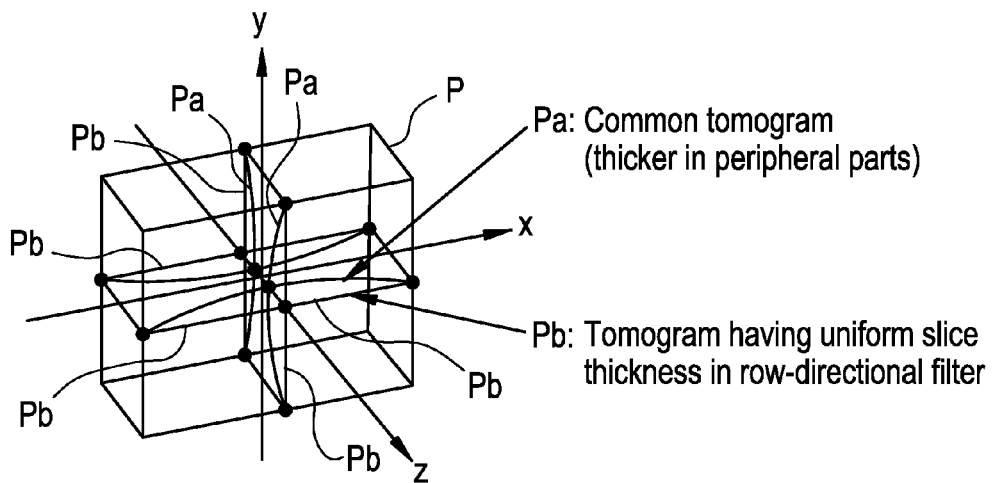
[FIG. 14]

Or as shown in FIG. 14 for instance, the slice thickness SLa is greater in the peripheral part than in the central part of reconstruction in a common CT tomogram PA.

On the other hand, in the row-directional filtering pertaining to the invention, it varies with the distance from channels in the central part as shown in FIG. 13 (b) for instance.

Figure 13B:
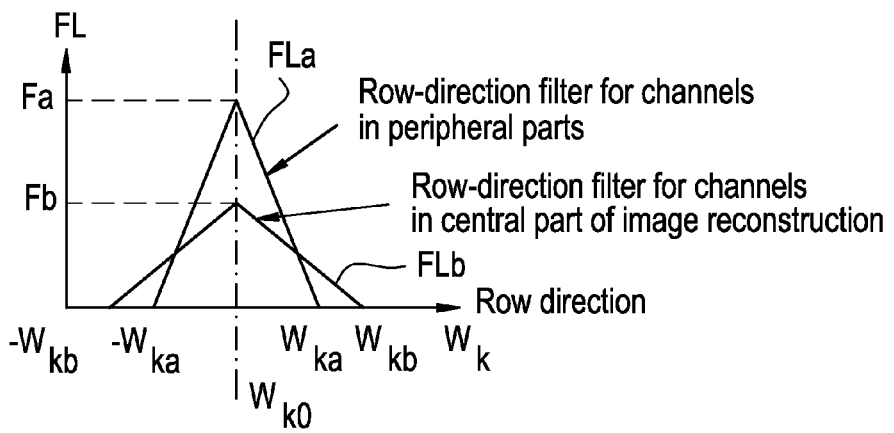

In more detail, the row-directional filter pertaining to the invention, as shown in FIG. 13(b) for instance, so processes row-directional filtering as to enlarge the filter coefficient in the central position as the distance from channels in the central part increases and to reduce the distance Wk where the filter coefficient becomes 0 on the basis of projection data on fewer rows near the peripheral parts than in the central part.

In this procedure, row-directional filtering may be processed with the filter coefficient FLa in the peripheral parts and with the filter FLb in the central part as shown in FIG. 13(b), or row-directional filtering may be processed with filter coefficients which smoothly and continuously vary from the filter coefficient FLa to the filter coefficient FLb according to the distance from the central position Wk0.

By doing so, it is made possible, where the row-directional filtering pertaining to the invention is used, as shown in FIG. 14 for instance, a tomogram p whose thickness is substantially uniform whether in the peripheral parts or in the central part of reconstruction can be subjected to image reconstruction.

By controlling the row-directional filter coefficients of channels in the central part and channels in the peripheral parts of the multi-row X-ray detector 24 in this way, the slice thickness can also be controlled in the central part and in the peripheral parts. By somewhat increasing the slice thickness in row-directional filtering, substantial improvement can be achieved in respect of both artifacts and noise. In this way, the extent of improvement in respect of artifacts and that in respect of noise can also be controlled. In other words, a tomogram having undergone three-dimensional image reconstruction, namely picture quality in the xy plane, can be controlled. Further, in still another mode for carrying out the invention, by using a deconvolution filter as the row-directional (z-directional) filter coefficient, a tomogram of thinner slice thickness can be realized as well.

At step S5, reconstructing function convolution is processed. Thus, a Fourier transform is done, multiplication by the reconstructing function is done, and an inverse Fourier transform is done. At S5 of reconstructing function convolution processing, the data after z-filter convolution processing being represented by D12, the data after reconstructing function convolution processing by D13 and the reconstructing function to be convoluted by Kernel (j), the reconstructing function convolution processing can be represented by Mathematical Expression (6) below.

[Mathematical Expression 6]

$$D13(view,j,i)=D12(view,j,i)*Kernel(j) \qquad (6)$$

Thus, since the reconstructing function kernel (j) permits independent reconstructing function convolution processing of each of the j detector rows, differences in noise characteristics and resolution characteristics from row to row can be corrected.

At step S6, the projection data D13 (view, j, i) having undergone reconstructing function convolution processing are subjected to three-dimensional back-projection to figure out back-projection data D3 (x, y). The image to undergo image reconstruction is subjected to three-dimensional image reconstruction on a plane orthogonal to the z-axis, namely the xy plane. The following reconstruction area P is supposed to parallel to the xy-plane. This three-dimensional back-projection processing will be described afterwards with reference to FIG. 5.

At step S7, the back-projection data D3 (x, y, z) undergo post-treatment including image filter convolution and the conversion of CT values to obtain a tomogram D31 (x, y).

In the image filter convolution of post-treatment, the three-dimensional back-projected tomogram being represented by D31 (x, y, z), the data having undergone image filter convolution, by D32 (x, y, z), and the image filter, by Filter (z), Mathematical Expression (7) below holds.

[Mathematical Expression 7]

$$D32(x,y,z)=D31(x,y,z)*Filter(z) \qquad (7)$$

Thus, since it permits independent convolution processing of each of the j detector rows, differences in noise characteristics and resolution characteristics from row to row can be compensated for.

The tomogram obtained is displayed on the monitor 6.

FIG. 5 is a flow chart showing details of the three-dimensional back-projection processing (step S6 in FIG. 4).

In this embodiment, the image to be reconstructed undergoes three-dimensional image reconstruction on a plane orthogonal to the z-axis, namely the xy plane. The following reconstruction area P is supposed to be parallel to the xy-plane.

At step S61, note is taken of one of all the views necessary for image reconstruction of a tomogram (namely the 360-degree view or "the 180-degree view+ the fan angle view"), and projection data Dr matching the pixels in the reconstruction area P are extracted.

Figure 6A:
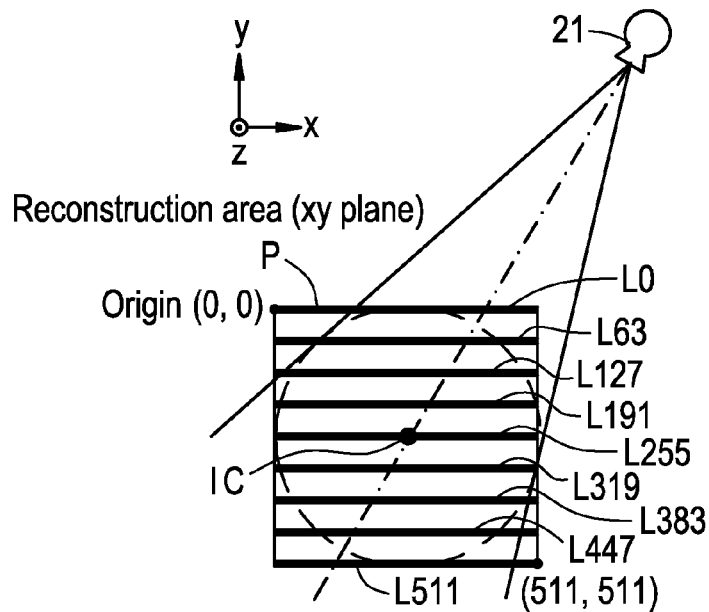
FIGS. 6a and 6b are conceptual diagrams showing the state of projecting lines on the reconstruction area in the X-ray transmitting direction.
Figure 6B:
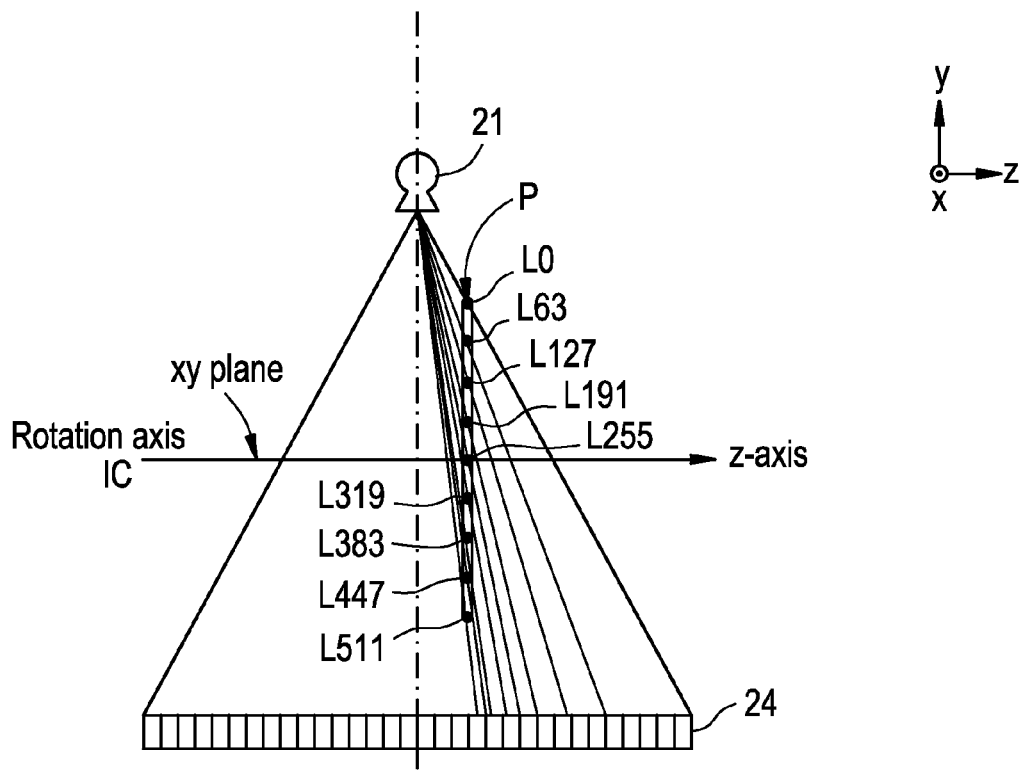
Figure 7:
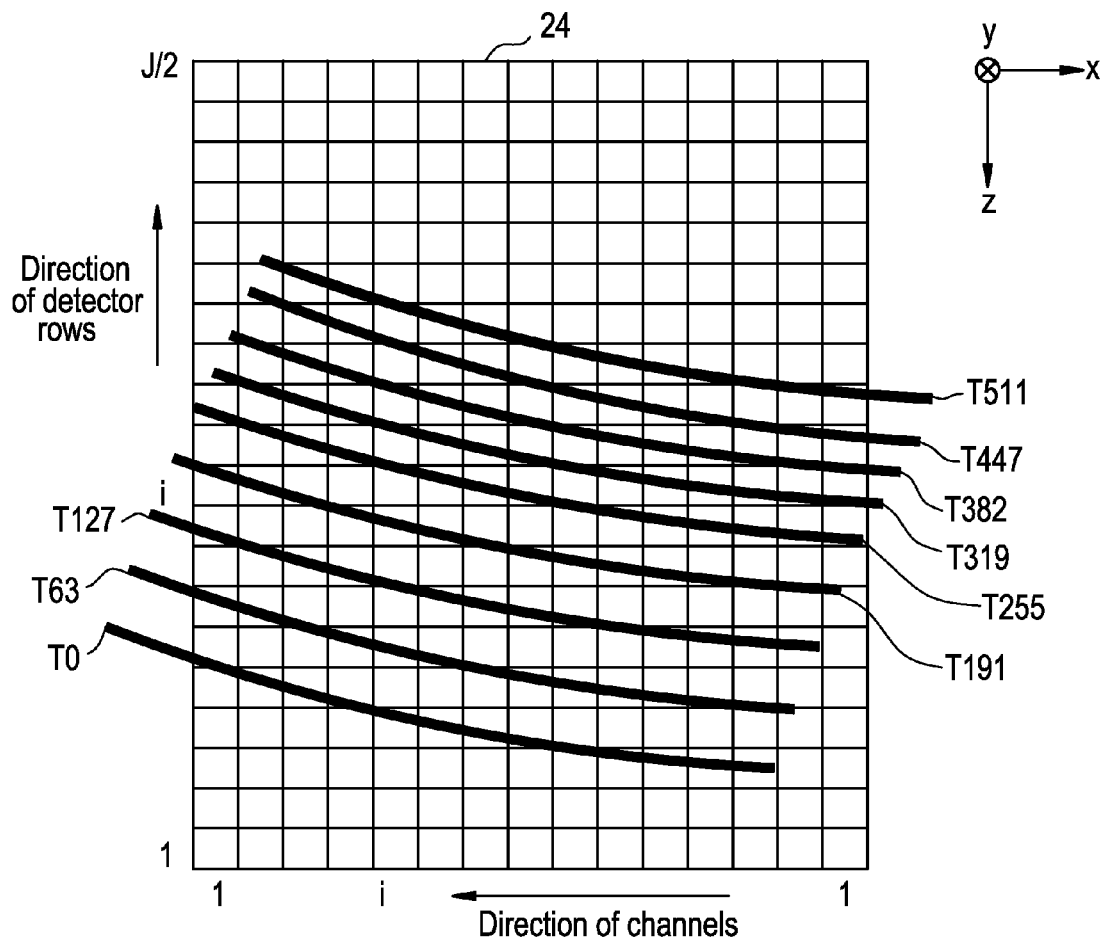
[FIG. 7]

As shown in FIGS. 6(a) and (b), a square area of 512×512 pixels parallel to the xy plane being chosen as the reconstruction area P with the rows comprising a pixel row L0 of y=0 parallel to the X-axis, a pixel row L63 of y=63, a pixel row L127 of y=127, a pixel row L191 of y=191, a pixel row L255 of y=255, a pixel row L319 of y=319, a pixel row L383 of y=383, a pixel row L447 of y=447 and a pixel row L511 of y=511, if projection data on lines T0 through T511 as shown in FIG. 7 wherein these pixel rows L0 through L511 are projected on the plane of the multi-row X-ray detector 24 in the X-ray transmitting direction are extracted, they will be the projection data Dr (view, x, y) of the pixel rows L0 through L511. It is to be noted that x and y match the pixels (x, y) of the tomogram.

Whereas the X-ray transmitting direction is determined by the geometric positions of the X-ray focus of the X-ray tube 21, the pixels and the multi-row X-ray detector 24, the z coordinate z (view) of the X-ray detector data D0 (view, j, i) is attached to the X-ray detector data as the linearly moving z-directional position Ztable (view) and therefore known, the X-ray transmitting direction can also be accurately figured out from the X-ray detector data D0 (view, j, i) during acceleration or deceleration in the data collecting geometric system of the X-ray focus and the multi-row X-ray detector.

Incidentally, when some of the lines goes out of the channel direction of the multi-row X-ray detector 24, as does line T0 resulting from the projection of the pixel row L0 for instance onto the plane of the multi-row X-ray detector 24 in the X-ray transmitting direction, the matching projection data Dr (view, x, y) are reduced to "0". Or if it goes out of the z-direction, it will be figured out by extrapolating the projection data Dr (view, x, y).

Figure 8:
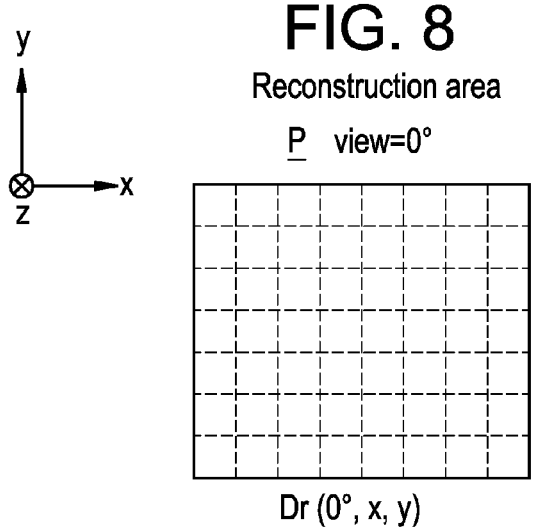
[FIG. 8]

In this way, the projection data Dr (view, x, y) matching the pixels of the reconstruction area P can be extracted as shown in FIG. 8.

Figure 9:
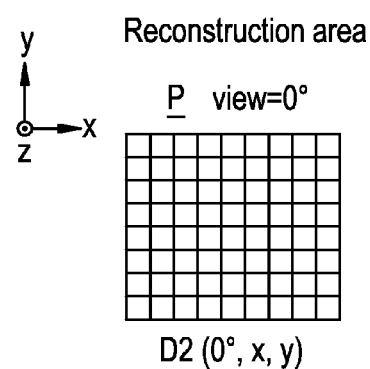
[FIG. 9]

Referring back to FIG. 5, at step S62, the projection data DT (view, x, y) are multiplied by a cone beam reconstruction weighting coefficient to create projection data D2 (view, x, y) as shown in FIG. 9.

The cone beam reconstruction weighting coefficient w (i, j) here is as follows. In the case of fan beam image reconstruction, generally the angle formed by a straight line linking at view=$\beta a$ the focus of the X-ray tube 21 and a pixel g (x, y) on the reconstruction area P (on the xy plane) to the central axis Bc of the X-ray beam is represented by $\gamma$ and its opposed view, by view=$\beta b$, $\beta b = \beta a + 180° - 2\gamma$ holds.

Where the angles formed by the X-ray beam passing the pixel g (x, y) on the reconstruction area P and its opposed X-ray beam with the reconstruction area P are represented by $\alpha a$ and $\alpha b$, they are multiplied by cone beam reconstruction weighting coefficients $\omega a$ and $\omega b$ dependent on them and the products are added; the back-projection pixel data D2 (0, x, y) are figured out on the basis of Equation (8) below.

$$D2(0,x,y) = (a(D2((0,x,y)(a+(b(D2(0,x,y)(b \quad (8)$$

In the foregoing, D2 (0, x, y)_a are the projection data of the view (a, and D2 (0, x, y)_b, the projection data of the view (b.

Incidentally, the sum of opposed beams of the cone beam reconstruction weighting coefficient is (a+(b=1.

By multiplying the cone beam reconstruction weighting coefficients (a and (b by each other and adding the products, cone angle artifacts can be reduced.

For instance, as the cone beam reconstruction weighting coefficients (a and (b, what are figured by the following equations can be used. Incidentally, ga is the weighting coefficient of a certain X-ray beam and gb, the weighting coefficient of the opposed X-ray beam.

Where ½ of the fan beam angle is represented by (max, the calculation is made on the basis of Equations (9) through (14). Here, q=1 is supposed for instance.

[Mathematical Expression 8]

$$ga = f(\gamma max, aa, \beta a) \quad (9)$$

$$gb = f(\gamma max, ab, \beta b) \quad (10)$$

$$xa = 2 \cdot ga^q / (ga^q + gb^q) \quad (11)$$

$$xb = 2 \cdot gb^q / (ga^q + gb^q) \quad (12)$$

$$wa = xa^2 \cdot (3 - 2xa) \quad (13)$$

$$wb = xb^2 \cdot (3 - 2xb) \quad (14)$$

If, as an example of ga and gb, max [ ] is supposed to be a function taking a greater value for instance, the following Equations (15) and (16) will hold.

[Mathematical Expression 9]

$$ga = \max[0, \{(\pi/2 + \gamma max) - |\beta a|\} \cdot |\tan(aa)|] \quad (15)$$

$$gb = \max[0, \{(\pi/2 + \gamma max) - |\beta b|\} \cdot |\tan(ab)|] \quad (16)$$

In the case of fan beam image reconstruction, each pixel on the reconstruction area P is multiplied by a distance coefficient. The distance coefficient is $(r1/r0)^2$ where r0 is the distance from the focus of the X-ray tube 21 to channel i of detector row j of the multi-row X-ray detector 24 matching the projection data Dr and r1, the distance from the focus of the X-ray tube 21 to a pixel on the reconstruction area P matching the projection data Dr.

In the case of parallel beam image reconstruction, each pixel on the reconstruction area P needs to be multiplied only by the cone beam reconstruction weighting coefficient w (i, j).

Figure 10:
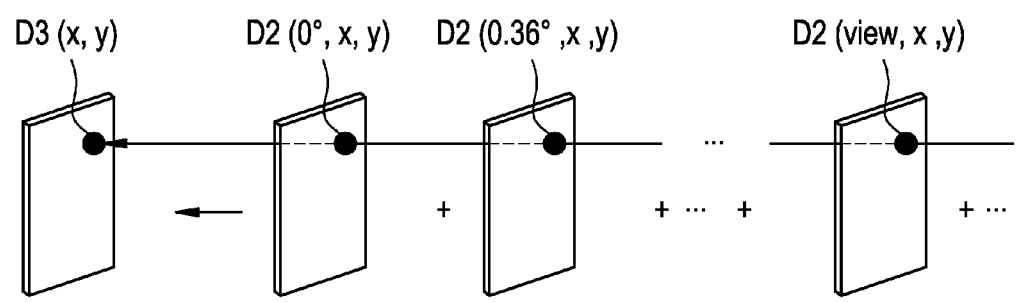
[FIG. 10]

At step S63, as shown in FIG. 10, the projection data D2 (view, x, y) are added, correspondingly to pixels, to the back-projection data D3 (x, y) which have been cleared in advance.

At step S64, steps S61 through S63 are repeated for all the views necessary for image reconstruction of a tomogram (namely the 360-degree view or "the 180-degree view+ the fan angle view") to obtain the back-projection data D3 (x, y) as shown in FIG. 10.

Figure 11A:
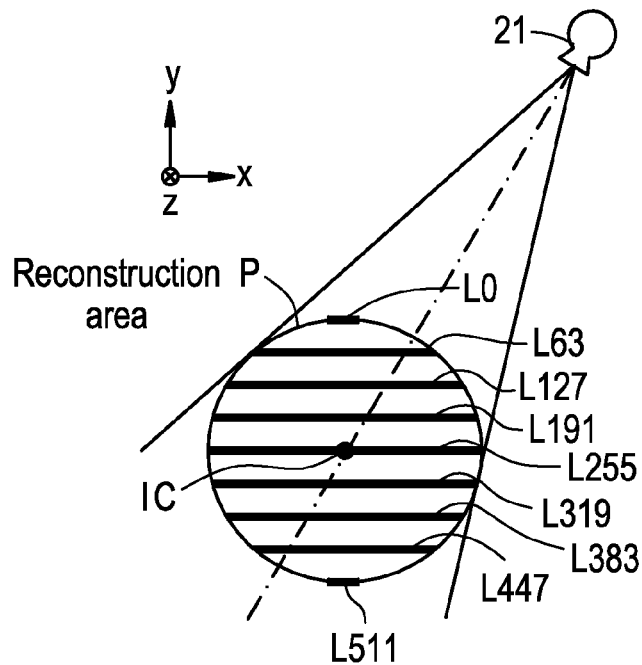
FIGS. 11a and 11b are conceptual diagrams showing the state of projecting lines on a round reconstruction area in the X-ray transmitting direction.
Figure 11B:
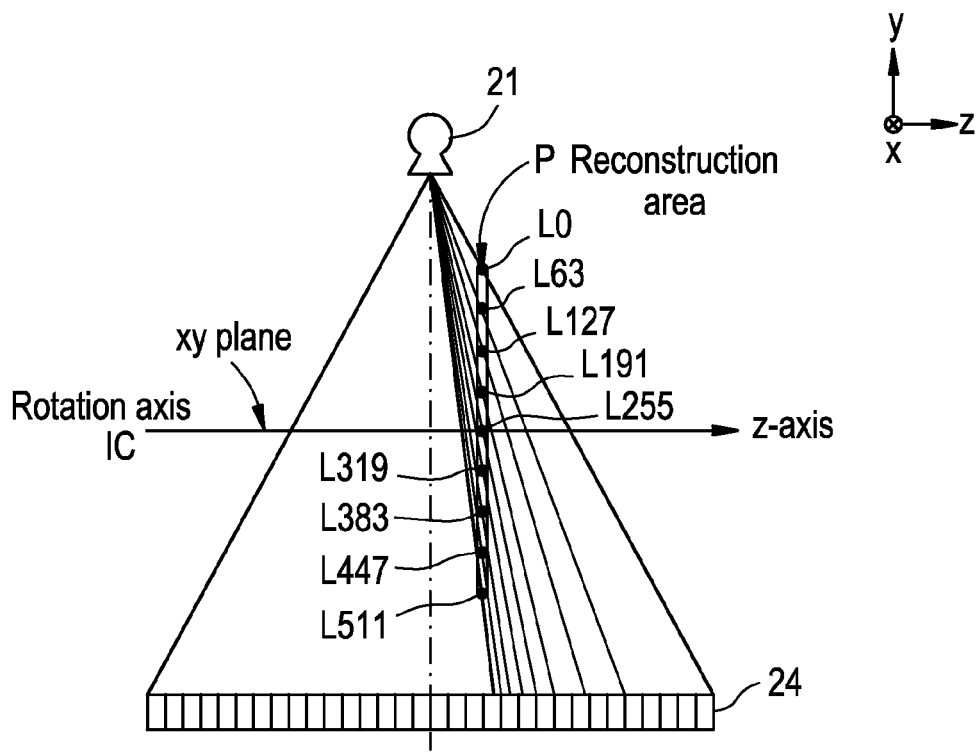

Incidentally, as shown in FIGS. 11(a) and (b), the reconstruction area P may be a round area of 512 pixels in diameter instead of a square area of 512 pixels×512 pixels.

In the basis three-dimensional image reconstruction so far described, the following contrivances are applied with a view to further improvement of picture quality.

In addition to the embodiment described above, arciform projection data are effectively utilized in three-dimensional image reconstruction hardware (or software) with no freedom, and improvement is made in respect of inconsistencies inherent in the conventional three-dimensional reconstruction algorithm or the Feldkamp image reconstruction algorithm to ameliorate the picture quality of tomograms.

In order to achieve the object stated above, it should be possible to create virtual arciform projection data in any desired position, and inconsistencies should be reduced by compressing the relative density of arciform projection data.

However, creation of virtual arciform projection data in any desired position cannot be realized with three-dimensional image reconstruction hardware (or software) with no freedom.

Further, as described above, three-dimensional image reconstruction hardware with no freedom can merely perform three-dimensional image reconstruction according to given views, helical pitch, width of the X-ray detector in the z-direction, number of slices and other items of information.

A method to resolve these mutually contradictory points will be described below.

Here it is considered replacement of given helical data with helical data of a different helical pitch.

This is a method of reconstructing an image by giving, for instance, information including a helical pitch matching virtual arciform projection data to three-dimensional image reconstruction hardware with no freedom.

In more detail, a greater dz would result in an increased density of the information of arciform projection data.

This characteristic is utilized to create virtual arciform projection data matching a greater helical pitch than the actual helical pitch.

A greater helical pitch device a greater dz. As a result, it is made possible to create denser virtual arciform projection data than the conventional real arciform projection data.

It is further possible to use these virtual arciform projection data and virtual helical pitch information to accomplish three-dimensional image reconstruction with these virtual arciform projection data as input.

In other words, this is to rearrange the helical data into helical data different in helical pitch.

Figure 28:
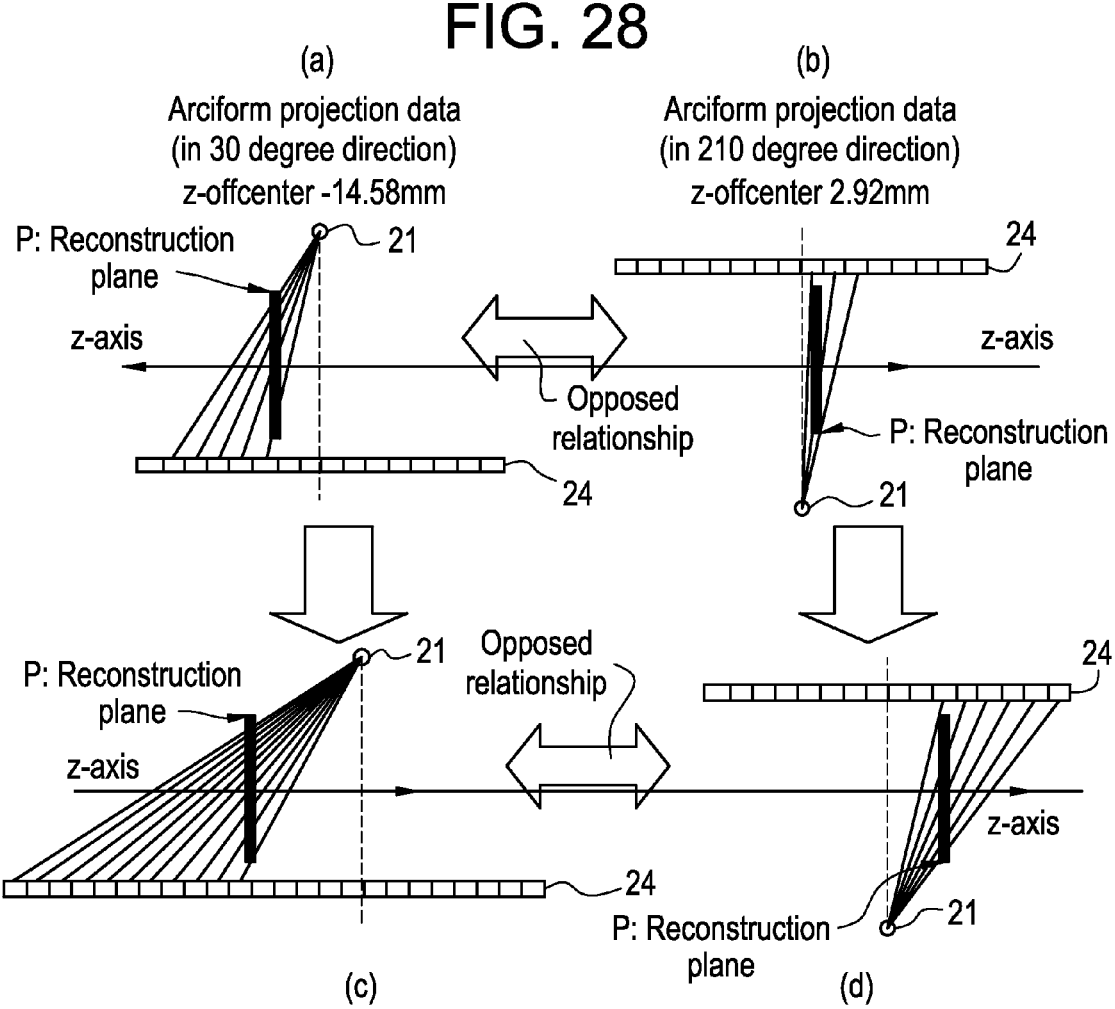
[FIG. 28]

More specifically, it is to rearrange two sets of projection data (helical data) shown in FIGS. 28(a) and (b) for instance into two opposed sets of projection data (helical data) differing in helical pitch as shown in FIGS. 28(c) and (d).

Figure 27:
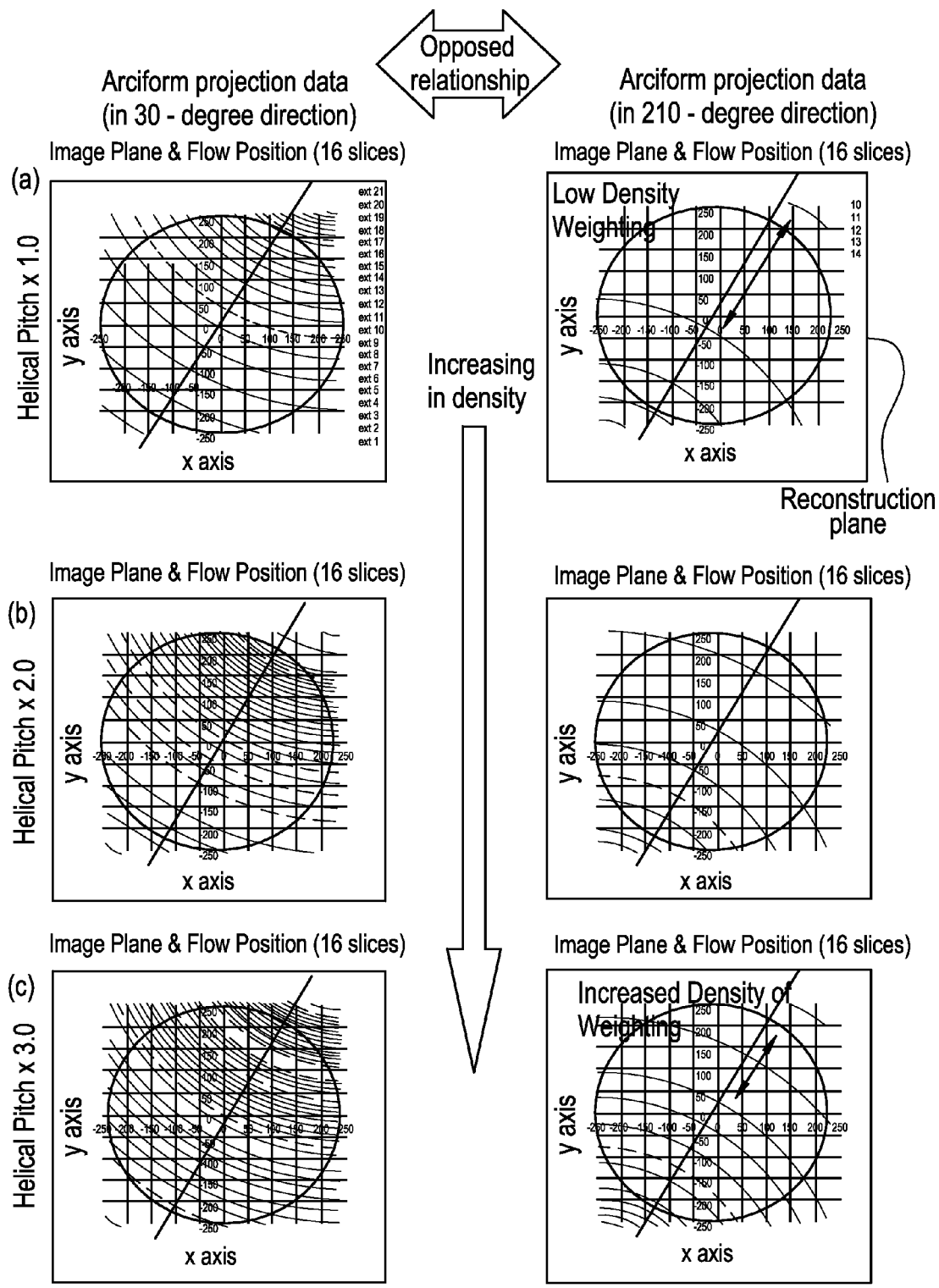
[FIG. 27]

What illustrate variations in the relative density of virtual arciform projection data differing in helical pitch by manipulation of helical pitch information are FIGS. 27(a) through (c) for instance.

FIG. 27(a) shows how arciform projection data whose view direction is at 30 degrees and arciform projection data opposed thereto whose view direction is at 210 degrees are projected on a reconstruction plane, where the helical pitch is 1.0. It is seen that, while the arciform projection data whose view direction is at 30 degrees are distributed with sufficient density, the arciform projection data in the 210-degree direction have few arcs on the reconstruction plane and sparse in distribution.

FIG. 27(b) shows how arciform projection data whose view direction is at 30 degrees and arciform projection data opposed thereto whose view direction is at 210 degrees are projected on a reconstruction plane, where the helical pitch is 2.0. The arciform projection data in the 30-degree direction are distributed even more densely on the reconstruction plane. It is seen that the arciform projection data in the 210-degree direction have slightly increased arcs on the reconstruction plane.

FIG. 27(c) shows how arciform projection data whose view direction is at 30 degrees and arciform projection data opposed thereto whose view direction is at 210 degrees are projected on a reconstruction plane, where the helical pitch is 3.0. The arciform projection data in the 30-degree direction are distributed still more densely on the reconstruction plane. It is seen that the arciform projection data in the 210-degree direction have further increased arcs on the reconstruction plane, sufficiently denser in distribution than in the case where the view direction is at 30 degrees and the helical pitch is 1.0.

As shown in FIGS. 27(a) through (c), by varying helical pitch information, even with three-dimensional image reconstruction hardware (or software) having no freedom, virtual arciform projection data can be created in any desired position though it has the constraint of a helical geometric system for X-ray data collection.

Also, by creating virtual arciform projection data as desired in this way, the relative density of virtual arciform projection data can be also controlled.

Figure 26:
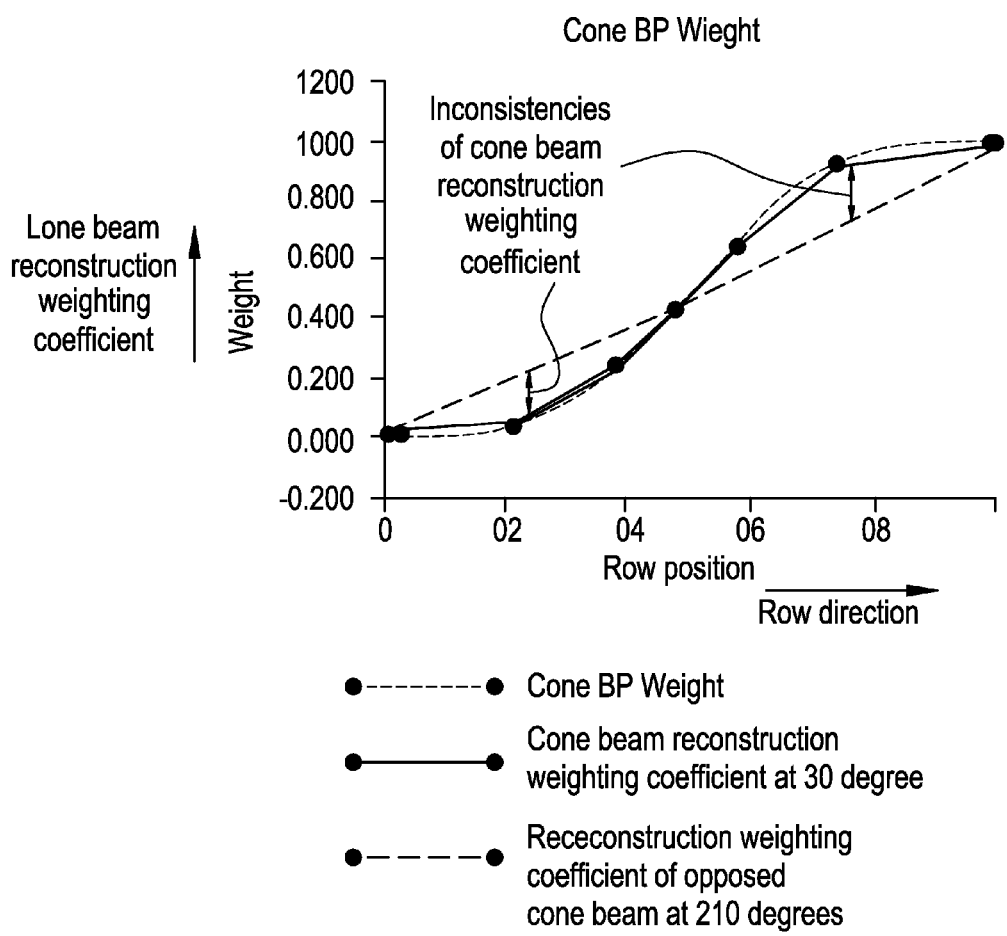
[FIG. 26]
Figure 29:
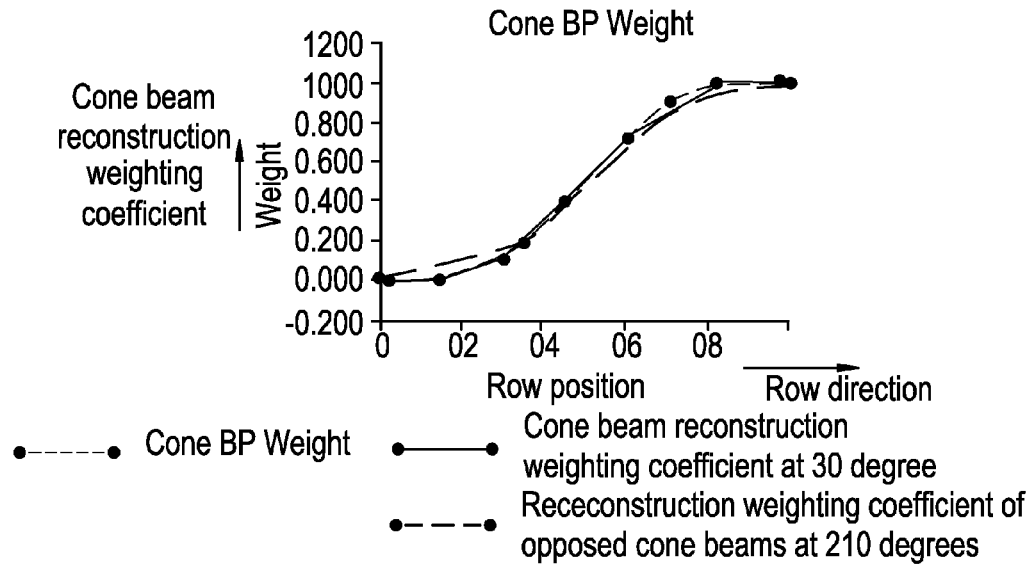
[FIG. 29]

Further, by controlling the relative density of virtual arciform projection data in this way, inconsistencies in the cone beam reconstruction weighting coefficients of three-dimensional image reconstruction due to differences in the density of opposed data as shown in FIG. 26 for instance can be reduced as shown in FIG. 29 for instance.

However, where virtual arciform projection data of a geometric system for X-ray data collection different from the actual helical pitch is created by controlling the helical pitch and three-dimensional image reconstruction hardware having no freedom is to used, it is impossible to alter the ratio of relative density of opposed data. In other words, the accuracy of images is dependent on the density of the less dense arciform projection data whose dz is smaller, and the arciform projection data with a greater dz will become denser than necessary, resulting in inferior data efficiency.

Next will be considered a case in which the helical data are replaced with conventional scanned projection data.

What will be considered is to eliminate difference in the relative density of virtual arciform projection data due to dz with a view to further improvement in respect of the problem noted above. Of course, since three-dimensional image reconstruction hardware has no freedom, this hurdle should be cleared, but its realization can be achieved by utilizing three-dimensional image reconstruction by conventional scanning (axial scanning) or cine scanning.

Conventional scanning (axial scanning) or cine scanning, unlike the helical, dz is constant in all the views.

Figure 30:
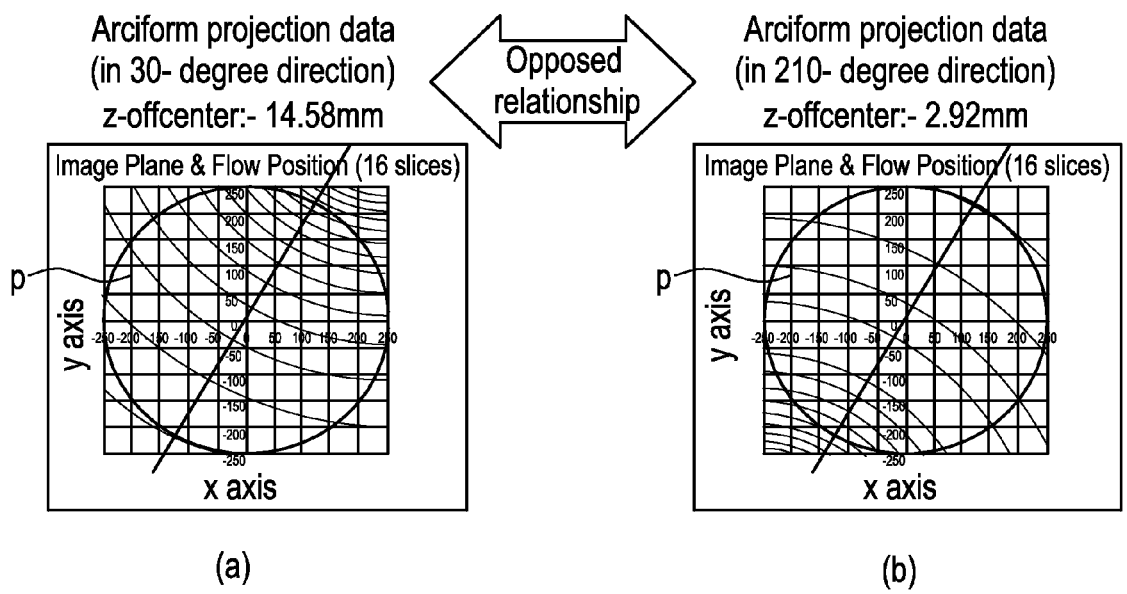
[FIG. 30]

Conversely, dz is received as a parameter input and this dz is applied to all the view data. It is illustrated on the xy plane as shown in FIGS. 30(a) and (b). It is expressed on the XZ plane as shown in FIGS. 31(a) through (d).

FIG. 30(a) shows how arciform projection data whose view direction is at 30 degrees and FIG. 30(b), how arciform projection data whose view direction is at 210 degrees, constituting opposed data, are projected on the reconstruction plane. It is seen that, by controlling dz, the distribution density of arciform projection data in the 30-degree direction on reconstruction plane and the distribution density of arciform projection data in the 210-degree direction on the reconstruction plane are made equal.

Figure 31:
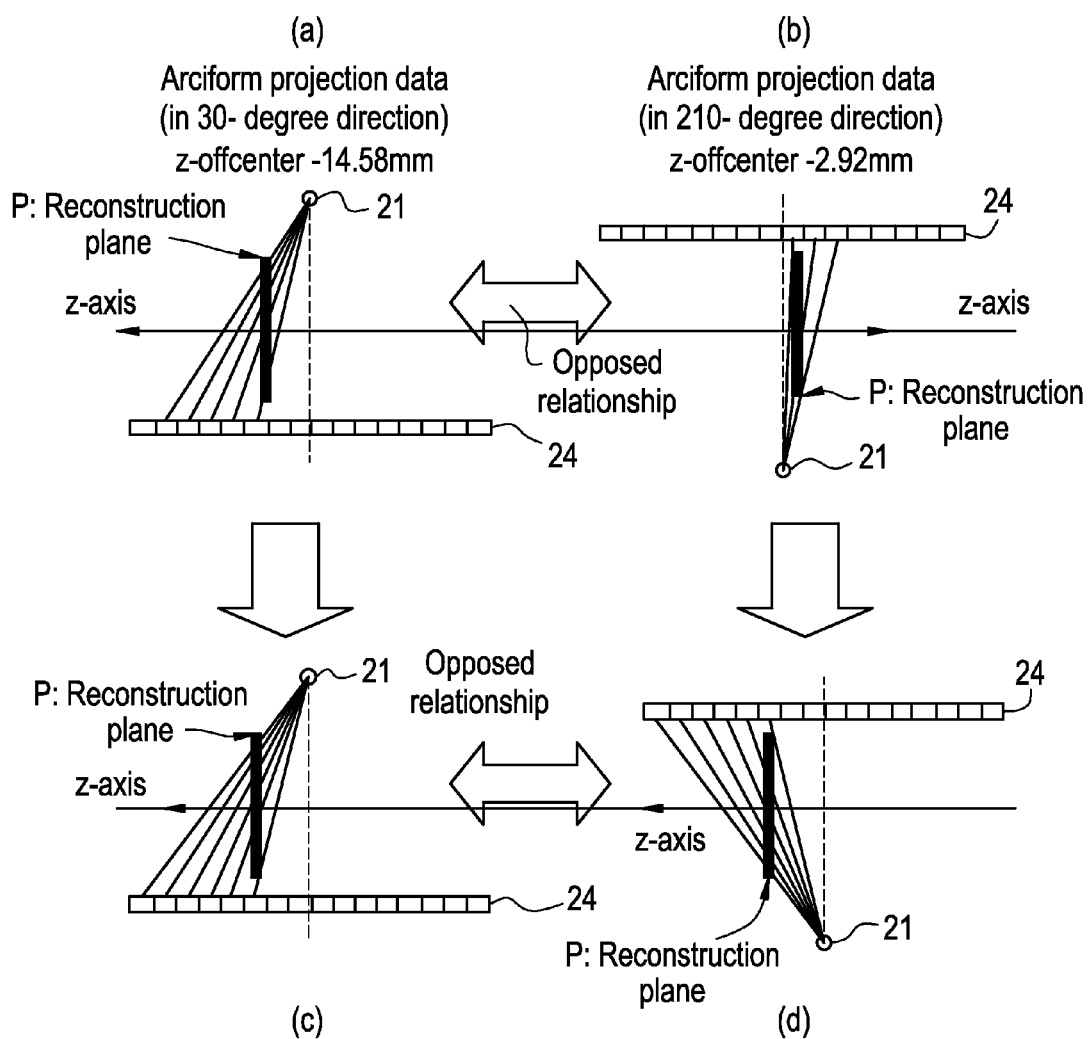
[FIG. 31]

FIG. 31(a) shows how arciform projection data whose view direction is at 30 degrees look and FIG. 31(b), how arciform projection data whose view direction is at 210 degrees, constituting opposed data, look as seen from the yz plane. It is seen that, by enlarging dz, the number of X-rays projected crossing the reconstruction plane is increased in the look of arciform projection data whose view direction is at 30 degrees in FIG. 31(c) and in that of arciform projection data whose view direction is at 210 degrees, constituting opposed data, in FIG. 31(d), as seen from the yz plane.

It is seen that, by controlling dz in this way, the distribution density of arciform projection data on the reconstruction plane can be controlled.

Thus even for sets of view data differing in dz, by virtually replacing dz with conventional data, control can be effected to uniformize the relative density of virtual arciform projection data.

In order to uniformize the relative density of virtual arciform projection data and at the same time to increase the overall density, the value of dz of virtual conventional scanning is raised.

Conversely, in order to reduce the data size and alleviate the loads of inputs/outputs by keeping the density low, the value of dz of virtual conventional scanning is lowered.

If the relative densities of sets of mutually opposed data are uniformized in this way, the aforementioned inconsistencies in weighting can be efficiently reduced.

By the two methods described above, virtual arciform projection data can be created in any desired position, and the level of their relative density can be controlled.

Also, the ratio of elative densities of sets of mutually opposed data can be uniformized.

Further, inconsistencies in weighting inherent in a common three-dimensional reconstruction algorithm or the Feldkamp image reconstruction algorithm and arciform projection data can be reduced, making it possible to qualitatively improve tomograms.

Also, though drawings of the present invention are prepared with basic focus on fan image reconstruction, the invention can well be applied to lateral beam image reconstruction as well.

Incidentally, the invention is not limited to these modes for implementation, but can be appropriately modified as desired.

The configurations and operations described are not limited to these modes for implementation.

The X-ray CT apparatus 100 so far described can make the slice thickness of a tomogram substantially uniform between its central part and peripheral parts as shown in FIG. 14 for instance.

Also, as shown in FIG. 13(*b*) for instance, by controlling the filter coefficients of row-directional filtering for channels in the central part and channels in the peripheral parts of the multi-row detector 24, the slice thickness can also be controlled between the central part and the peripheral parts.

Further, the improvement in respect of artifacts and the improvement in respect of noise can also be controlled. In other words, the picture quality of tomograms having undergone three-dimensional image reconstruction can be controlled.

Incidentally, the method of image reconstruction may also be a three-dimensional image reconstruction method by the Feldkamp image reconstruction technique.

Furthermore, the three-dimensional image reconstructing methods disclosed in JP-A No. 2004-73360, JP-A No. 2003-33418, JP-A No. 2003-159244, JP-A No. 2004-41674 and so forth or other known three-dimensional image reconstructing method can as well be used. The point is to process image reconstruction by using the row-directional filter according to the invention.

Other conceivable modes for implementation include adjustment of fluctuations in picture quality by convoluting row-directional filtering differing in filter coefficient from row to row for instance thereby to realize uniformity in slice thickness and picture quality in terms of artifacts and noise from row to row; various z-direction filter coefficients are conceivable in this respect, and they would provide similar effects to these embodiments. These embodiments have been described with respect to X-ray CT apparatuses for medical use, but they can also be utilized as X-ray CT apparatuses for industrial use or as X-ray CT-PET apparatuses or X-ray CT-SPECT apparatuses in combination with other devices.

The invention claimed is:

1. An image reconstructing method for reconstructing a tomogram based on projection data collected by a multi-row X-ray detector for detecting X-rays radiated from the X-ray generating device, the image reconstructing method comprising:

performing a three-dimensional back-projection process based on the projection data, the three-dimensional back-projection process comprising convolving a row-directional filter on the projection data, the row-directional filter having a filter coefficient that differs in a channel direction of the multi-row X-ray detector.

2. The image reconstructing method according to claim 1, further comprising:

convolving a reconstructing function on the obtained data by convolving a row-directional filter function on the projection data; and reconstructing by performing a three-dimensional back-projection process based on the data obtained by the reconstructing function.

3. The image reconstructing method according to claim 1, further comprising:

convolving a reconstructing function on the projection data;

convolving a row-directional filter on the data obtained by convolving the reconstructing function; and reconstructing by performing a three-dimensional back-projection process based on the data obtained by convolving the row-directional filter.

4. An X-ray CT apparatus comprising:

an X-ray generating device;

a multi-row X-ray detector which detects X-rays radiated from said X-ray generating device;

a data collecting device which collects projection data by rotating said X-ray generating device and said multi-row X-ray detector around a center of rotation between said X-ray generating device and said multi-row X-ray detector;

a row-directional filtering device for filtering the projection data by convolving a row-directional filter using a filter coefficient that differs in a channel direction of said multi-row X-ray detector on the projection data; and a back-projecting device for reconstructing a tomogramic view by three-dimensional back projecting the projection data obtained by said row-directional filtering device.

5. The X-ray CT apparatus according to claim 4, wherein said data collecting device collects data by conventional scanning, helical scanning or cine scanning.

6. The X-ray CT apparatus according to claim 4, wherein a filter coefficient of said row-directional filter is a deconvolution filter.

7. The X-ray CT apparatus according to claim 4, wherein said back-projecting device processes weighted addition in a row direction by one of linear weighted addition, multi-point weighted addition, and weighted addition with a nonlinear weighting coefficient.

8. The X-ray CT apparatus according to claim 4, wherein said three-dimensional back-projection device including back-projecting projection data of a virtualized X-ray detector row.

9. The X-ray CT apparatus according to claim 4, wherein the projection data of an X-ray detector row and the projection data of a virtualized X-ray detector row projection data are combined by row-directional filtering on a reconstruction plane in said three-dimensional back-projection process, and the process is proceeded so as to substantially equalize an interval on a reconstruction plane with the data in a given direction and an interval on the reconstruction plane in a direction opposed by 180 degrees.

10. The X-ray CT apparatus according to claim 9, wherein a total number of projected data rows combining a number of projection data of said X-ray detector rows and a number of projection data of the virtualized X-ray detector rows is optimized in each projection direction and 180 degrees to the projecting direction or the direction opposed by substantially 180 degrees.

11. The X-ray CT apparatus according claim 9, wherein a total number of projection data rows combining a number of projection data of said X-ray detector rows and a number of projection data of the virtualized X-ray detector rows is unified to a maximum number of each projecting direction in all of the projecting directions.

12. The X-ray CT apparatus according to claim 4, further comprising a reconstruction convolving device for convolving a reconstructing function on the projection data obtained by said row-directional filtering device, wherein said back-projecting device reconstructs a tomogramic view by three-dimensional back projecting the projection data obtained processing by said reconstruction convolving device.

13. The X-ray CT apparatus according to claim 4, further comprising a reconstruction convolving device for convolving a reconstructing function on the projection data collected by said data collecting device, wherein said row-directional filtering device convolves said row-directional filter in the row direction based on the projected data obtained by said reconstruction convoluting device.

* * * * *